United States Patent
Hasegawa et al.

(10) Patent No.: US 7,796,242 B2
(45) Date of Patent: Sep. 14, 2010

(54) INFORMATION IDENTIFICATION DEVICE, INFORMATION IDENTIFICATION METHOD, AND INFORMATION IDENTIFICATION SYSTEM

(75) Inventors: Yasuchika Hasegawa, Ikoma (JP); Tsuyoshi Kawai, Ikoma (JP)

(73) Assignees: National University Corporation, Ikoma-Shi Nara (JP); Nara Institute of Science and Technology, Ikoma-Shi Nara (JP)

( * ) Notice: Subject to any disclaimer, the term of this patent is extended or adjusted under 35 U.S.C. 154(b) by 278 days.

(21) Appl. No.: 11/990,604

(22) PCT Filed: Aug. 22, 2006

(86) PCT No.: PCT/JP2006/316385

§ 371 (c)(1),
(2), (4) Date: Feb. 19, 2008

(87) PCT Pub. No.: WO2007/023799

PCT Pub. Date: Mar. 1, 2007

(65) Prior Publication Data

US 2009/0224048 A1    Sep. 10, 2009

(30) Foreign Application Priority Data

Aug. 22, 2005  (JP) .............................. 2005-239452

(51) Int. Cl.
*G06K 9/74* (2006.01)
(52) U.S. Cl. ...................................................... 356/71
(58) Field of Classification Search .................... 356/71
See application file for complete search history.

(56) References Cited

U.S. PATENT DOCUMENTS 7,129,506 B2 * 10/2006 Ross et al. .................. 250/556

FOREIGN PATENT DOCUMENTS

| JP | 2002-046339 | 2/2002 |
|----|-------------|--------|
| JP | 2003-277659 | 10/2003 |
| JP | 2005-111704 | 4/2005 |
| JP | 2005-112947 | 4/2005 |
| JP | 2005-114909 | 4/2005 |

* cited by examiner

*Primary Examiner*—Michael P Stafira
(74) *Attorney, Agent, or Firm*—Harness, Dickey & Pierce, P.L.C.

(57) ABSTRACT

In one embodiment of the present invention, an information identification device, an information identification method, and an information identification system each of which can maintain a high security level and which can be used for a long time without any restrictions on use conditions are realized. An ID identification system includes: an ID identifying medium containing a rare-earth complex; and an ID identification device for identifying identification information corresponding to the rare-earth complex. The ID identification device includes: a light source for irradiating, with exciting light, an ID identifying medium containing a rare-earth complex; a measurement section for receiving light emitted from the ID identifying medium, and for measuring spectral intensities of the light; a computation section for computing a ratio of spectral intensities at different wavelengths among the spectral intensities thus measured; and an identification section for identifying identification information corresponding to the ratio thus computed.

12 Claims, 8 Drawing Sheets

FIG. 3

| LIR(Eu) | RARE-EARTH COMPLEX | ID |
|---|---|---|
| 6 | $Eu(HFA-D)_3(D_2O)_2(DMSO-d_6)_n$ | A |
| 8 | $Eu(HFA-D)_3(TPPO)_2(DMSO-d_6)_n$ | B |
| 12 | $Eu(HFA-D)_3(D_2O)_2$ | C |
| 17 | $Eu(HFA-D)_3(TPPO)_2$ | D |
| 18 | $Eu(HFA-D)_3(TPPO-F)_2$ | E |

F I G. 9
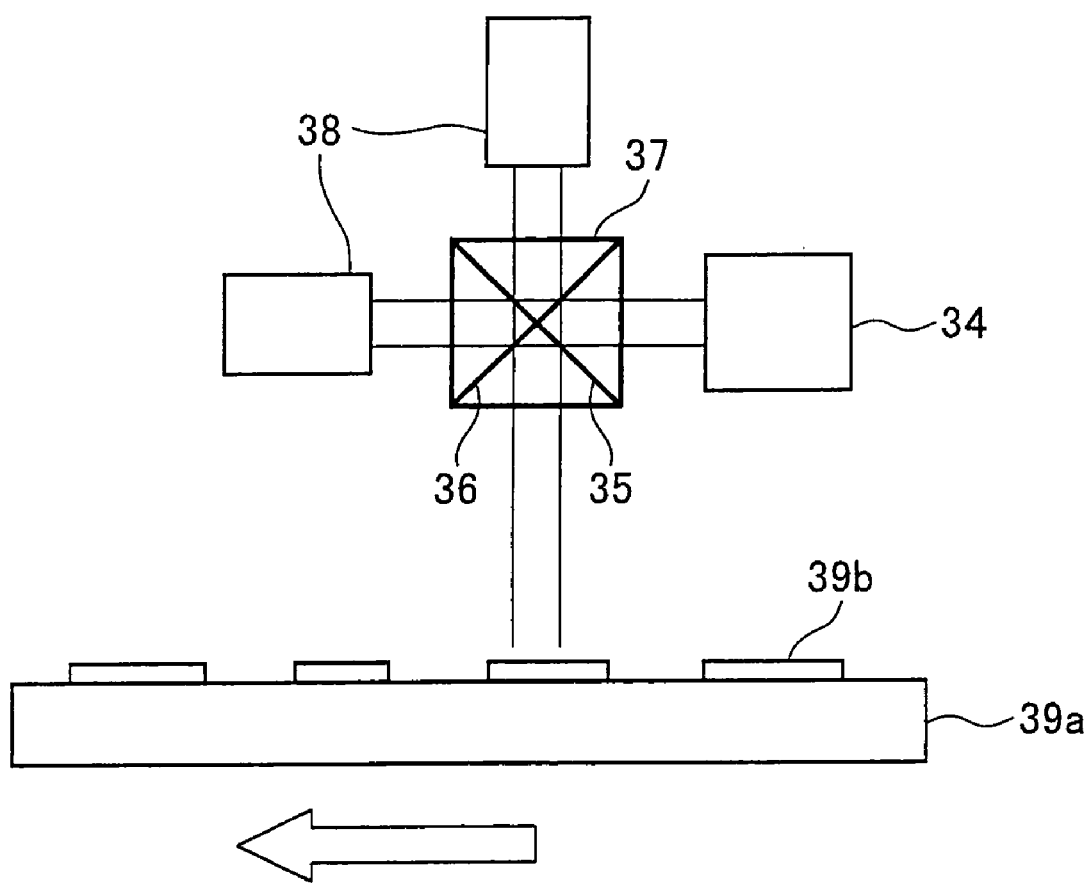

INFORMATION IDENTIFICATION DEVICE, INFORMATION IDENTIFICATION METHOD, AND INFORMATION IDENTIFICATION SYSTEM

TECHNICAL FIELD

The present invention relates to information identification devices, information identification methods, and information identification systems. More specifically, the present invention relates to an information identification device, an information identification method, and an information identification system each of which identifies identification information by identifying (specifying) a rare-earth complex by calculating the ratio of intensities of light emitted from the rare-earth complex at different wavelengths.

BACKGROUND ART

Conventionally, authentication systems using IDs have been utilized in various fields. Among them, security systems have been widely used, for example, for preventing leakages of personal information, for controlling entrance into and exit from buildings, and for preventing forgery of documents and luxuries. That is, security systems based on advanced ID authentication are important technologies for ensuring "safety" and "security" in the 21st century society.

Examples of ID recognition methods used in conventional security systems include ID recognition methods based on material information (e.g., keys, magnetic cards, IC cards, and bar codes printed in luminescent ink), ID recognition methods based on human information (e.g., fingerprints, voice recognition, and face recognition), and ID recognition methods based on passwords (i.e., encryption of digital information).

However, these ID recognition methods have the following problems. For example, the ID recognition methods based on material information cannot completely deny the possibility of forgery or reproduction of materials. Further, the ID recognition methods based on human information reduce the precision of ID recognition due to differences in voices and faces among people. Further, information may be forged with use of a fingerprint tape, a photograph, or the like. Furthermore, the ID recognition methods based on passwords cannot completely deny the possibility of hacking since the methods use digital information.

Therefore, in order to overcome these problems, it is necessary to use technologies that perform more advanced ID recognition. Examples of such technologies include technologies using advanced-information recording materials. Further, examples of such technologies using advanced-information recording materials include technologies using light emitters. In this case, a plurality of light emitters are used for encryption. That is, an ID is authenticated in accordance with the intensity of light emitted from each of the light emitters.

Examples of the other technologies using light emitters include technologies related to identifying marks made with light emitters (such technologies being disclosed, for example, in Patent Documents 1 to 3). Patent Documents 1 to 3 disclose technologies related to identifying marks made with rare-earth complexes. Each of these patent documents uses an optically-active rare-earth complex, and checks the authenticity of an identifying mark by calculating the intensity difference between a right-handed circularly polarized component and left-handed circularly polarized component of fluorescence emitted from the optically-active rare-earth complex and by determining whether or not the intensity difference is 0.

However, the plurality of light emitters differ from one another in the rates at which the light emitters deteriorate due to light and heat and in the luminescence properties of the light emitters with respect to temperature. For this reason, the technology for measuring the intensity of light emitted from each of the light emitters and authenticating (identifying) an ID in accordance with the intensity causes variations in intensity due to differences among the light emitters in the rates at which the light emitters deteriorate and in the temperature characteristics of the light emitters. This causes errors in identification, thereby imposing restrictions on use conditions and making long-term use difficult.

Further, each of the technologies described in the foregoing patent documents checks the authenticity of an identifying mark simply by measuring the presence or absence of circularly-polarized light. For this reason, the technologies can be used for preventing forgery of pieces of paper money and securities. However, the technologies are inappropriate for identification and authentication of identification information such as IDs for the following reasons: (1) There are scarcities in types of optically-anisotropic complex; (2) It is more difficult to purify an optically-anisotropic complex than to purify a normal complex; and (3) An optically-anisotropic complex is at least 2000 times as expensive as a rare-earth complex that is not optically active.

Patent Document 1: Japanese Unexamined Patent Application Publication No. 111704/2005 (Tokukai 2005-111704; published on Apr. 28, 2005)

Patent Document 2: Japanese Unexamined Patent Application Publication No. 112947/2005 (Tokukai 2005-112947; published on Apr. 28, 2005)

Patent Document 3: Japanese Unexamined Patent Application Publication No. 114909/2005 (Tokukai 2005-114909; published on Apr. 28, 2005)

DISCLOSURE OF THE INVENTION

The present invention has been made in view of the foregoing problems, and it is an object of the present invention to realize an information identification device, an information identification method, and an information identification system each of which maintains a high level of security by preventing leakages of identification information such as IDs and enables long-term use without any restrictions imposed on use conditions and without any influence of deterioration in material.

In order to solve the foregoing problems, an information identification device according to the present invention includes: a light source for irradiating, with exciting light, a light-emitting member containing a rare-earth complex; a measurement section for receiving light emitted from the light-emitting member, and for measuring spectral intensities of the light; a computation section for computing a ratio of spectral intensities at a plurality of different wavelengths among the spectral intensities thus measured; and an identification section for identifying identification information corresponding to the ratio thus computed.

According to the foregoing arrangement, the light-emitting member contains a rare-earth complex. For this reason, when the light source irradiates the light-emitting member with exciting light, the light-emitting member emits light. The measurement section receives the light emitted from the light-emitting member, and measures spectral intensities of the light. Further, the computation section computes a ratio of spectral intensities at a plurality of different wavelengths among the spectral intensities thus measured. That is, the computation section computes a ratio of intensities of line spectra at specific wavelengths. Then, the identification section identifies identification information corresponding to the ratio thus computed.

The measurement section may measure the intensities of one or more line spectra, and there may be provided a plurality of such measurement sections. The term "line spectrum" refers to a spectrum specified during transition between certain levels, and the term "spectra" refers to the whole of emitted light or a plurality of line spectra.

Thus, the present invention identifies the identification information corresponding to the rare-earth complex. That is, in general, a rare-earth complex has a plurality of emission line spectra that include an emission line spectrum based on magnetic dipole transition and an emission line spectrum based on electric dipole transition. The emission line spectrum based on magnetic dipole transition has a light intensity unique to the rare-earth complex. The emission line spectrum based on electric dipole transition has an intensity that varies depending on the type of ligand surrounding the rare-earth element, and has an intensity unique to the type of rare-earth complex. Therefore, the intensity ratio of the emission line spectrum based on electric dipole transition to the emission line spectrum based on magnetic dipole transition takes on a value unique to the rare-earth complex. For this reason, the rare-earth complex contained in the light-emitting member can be identified (specified) by measuring the intensities of line spectra at a plurality of different wavelengths based on the two types of transition among the light emitted from the rare-earth complex and by computing the ratio. This makes it possible to identify and authenticate the identification information corresponding to the rare-earth complex. Thus, the rare-earth complex contained in the light-emitting member can be identified, and an information identification device having an unprecedentedly high level of identifying power (security) can be provided by using the type of rare-earth complex for identification and authentication.

The "line spectra at a plurality of wavelengths" also means "a plurality of line spectra at different wavelengths". Therefore, "to compute an intensity ratio of line spectra at a plurality of wavelengths" means "to compute an intensity ratio of two or more line spectra at different wavelengths". That is, in this case, the computation section may compute an intensity ratio of line spectra at two wavelengths, an intensity ratio of line spectra at three wavelengths, or an intensity ratio of line spectra at four or more wavelengths. This can be appropriately set in accordance with the number of emission peaks of a rare-earth complex.

Further, since the present invention identifies a substance in accordance with the ratio of intensities of optical spectra that vary in proportion to the degree of deterioration, the substance can be identified even in cases where the rare-earth complex has deteriorated. There are no restrictions on use conditions such as temperature, either. The ratio of intensities of emission spectra of a rare-earth complex stays constant regardless of the degree of deterioration of the substance, and the temperature dependence varies from one rare-earth complex to another and does not vary depending on the wavelengths of the emission spectra of the rare-earth complex.

Further, the rare-earth complex is transparent and colorless and therefore invisible when not in use (when not irradiated with exciting light), thereby ensuring a higher level of security. Furthermore, the use of a single rare-earth ion makes it possible to recover used rare-earth ions, which are precious resources.

The information identification device according to the present invention is preferably arranged so as to further include a wavelength selection section for splitting, into spectra containing a first-wavelength line spectrum and spectra containing a second-wavelength line spectrum, the light emitted from the light-emitting member, wherein the measurement section measures intensities of the spectra that have been split by the wavelength selection section.

The wavelength selection section selects light at a specific wavelength from among the light emitted from the light-emitting member. The information identification device according to the present invention can further include a plurality of such wavelength selection sections for beams of light at different wavelengths. When arranged so as to include such wavelength selection sections, the information identification device according to the present invention can use the wavelength selection sections to select line spectra at different wavelengths from among the light emitted from the light-emitting member, respectively.

The line spectra respectively selected by the wavelength selection sections are line spectra of wavelengths that are measured for the purpose of computing an intensity ratio. That is, the measurement section measures the intensity of each of the line spectra respectively selected by the wavelength selection sections.

Thus, in cases where the wavelengths for computing an intensity ratio of line spectra are predetermined, the provision of wavelength selection sections for respective wavelengths makes it only necessary for the measurement section to measure only the intensity of a line spectrum at each wavelength. This makes it possible to increase the speed of processing, and to provide an information identification device having a higher level of identifying power (security).

The first-wavelength line spectrum and the second-wavelength line spectrum are line spectra at specific wavelengths among the light emitted from the light-emitting member. That is, the first-wavelength line spectrum and the second-wavelength line spectrum are a line spectrum based on magnetic dipole transition or a line spectrum based on electric dipole transition. The first-wavelength line spectrum and the second-wavelength line spectrum are spectra of wavelengths that are measured for the purpose of computing a light intensity ratio.

These line spectra at respective wavelengths are appropriately set in accordance with the emission distribution of the rare-earth complex, and are preferably any of the plurality of emission spectra. Thus, the ratio is computed in accordance with the intensities of light at two specific wavelengths. This not only makes it possible to identify the rare-earth complex, but also makes it easy to perform the computation.

Thus, since the first- and second-wavelength line spectra for computing an intensity ratio of line spectra can be determined in advance, it becomes only necessary to use the wavelength selection sections to split the spectra containing the first- and second-wavelength line spectra and to measure the intensity of each spectrum. This makes it possible to increase the speed of processing, and to provide an information identification device having a higher level of identifying power (security).

In other words, the information identification device according to the present invention is preferably arranged so as to include one or more wavelength selection sections, thereby splitting, into spectra containing a first-wavelength line spectrum and spectra containing a second-wavelength line spectrum, the light emitted from the light-emitting member, wherein: the measurement section measures respective intensities of the spectra containing the first-wavelength line spectrum and the spectra containing the second-wavelength line spectrum; and the computation section computes a ratio between the intensity of the spectra containing the first-wavelength line spectrum and the intensity of the spectra containing the second-wavelength line spectrum.

Furthermore, the information identification device according to the present invention is preferably arranged such that: the plurality of wavelength selection sections include a first wavelength selection section for splitting a first-wavelength line spectrum emitted from the light-emitting member and a second wavelength selection section for splitting a second-wavelength line spectrum emitted from the light-emitting member; the measurement section measures respective intensities of the first-wavelength line spectrum and the second-wavelength line spectrum; and that the computation section computes a ratio between the intensity of the first-wavelength line spectrum and the intensity of the second-wavelength line spectrum.

According to the foregoing arrangement, the wavelength selection sections include the first wavelength selection section and the second wavelength selection section. The first wavelength selection section splits the first-wavelength line spectrum emitted from the light-emitting member. Further, the second wavelength selection section splits the second-wavelength line spectrum emitted from the light-emitting member. The first-wavelength line spectrum and the second-wavelength line spectrum refer to those line spectra at specific wavelengths which are contained in the light emitted from the rare-earth complex, and to line spectra of wavelengths that are measured for the purpose of computing an intensity ratio of line spectra.

The measurement section measures the respective intensities of the first-wavelength line spectrum and the second-wavelength line spectrum. Further, the computation section computes the ratio between the intensity of the first-wavelength line spectrum and the intensity of the second-wavelength line spectrum. That is, the computation section computes the ratio of intensities of line spectra at two wavelengths for computing an intensity ratio of line spectra. Then, the identification section identifies the identification information corresponding to the ratio thus computed.

Thus, in cases where the two wavelengths for computing an intensity ratio of line spectra are determined, the provision of wavelength selection sections for respective wavelengths makes it only necessary for the measurement section to measure only the intensity of a line spectrum at each wavelength. Further, the computation section does not need to extract the intensities of line spectra at specific wavelengths from among all wavelengths, and can compute a ratio by using only the intensities of line spectra thus measured by the measurement section. This makes it possible to increase the speed of processing, and to provide an information identification device having a higher level of identifying power (security).

The information identification device according to the present invention is preferably arranged such that the wavelength selection section splits, by transmission, reflection, diffraction, or refraction, the light emitted from the light-emitting member.

The information identification device according to the present invention is preferably arranged such that the computation section computes a ratio between the intensity of the spectra containing the first-wavelength line spectrum and the intensity of the spectra containing the second-wavelength line spectrum among the spectral intensities measured by the measurement section.

The first-wavelength line spectrum and the second-wavelength line spectrum refer to those line spectra at specific wavelengths which are contained in the light emitted from the rare-earth complex, and to spectra of wavelengths that are measured for the purpose of computing a spectral intensity ratio.

These line spectra at respective wavelengths are appropriately set in accordance with the emission distribution of the rare-earth complex, and are preferably any of the plurality of emission spectra. Thus, the ratio is computed in accordance with the intensities of light at two specific wavelengths. This not only makes it possible to identify the rare-earth complex, but also makes it easy to perform the computation.

Further, the information identification device according to the present invention is preferably arranged such that the first-wavelength line spectrum is a line spectrum based on magnetic dipole transition and the second-wavelength line spectrum is a line spectrum based on electric dipole transition.

The information identification device according to the present invention is preferably arranged such that the light-emitting member contains plural types of rare-earth complex; and the computation section computes a ratio of spectral intensities at a plurality of wavelengths corresponding to each rare-earth complex.

According to the foregoing arrangement, each of the rare-earth complexes contained in the light-emitting member emits light. Moreover, the computation section computes a ratio of spectral intensities at wavelengths corresponding a spectrum emitted from each rare-earth complex. That is, although wavelengths of spectra for computing a ratio vary from one rare-earth complex to another, the computation section computes a ratio in accordance with spectral intensities at wavelengths for identifying each rare-earth complex. Therefore, even in cases where the plural types of rare-earth complex are used, each of the rare-earth complexes can be identified. This makes it possible to provide an information identification device having a higher level of identifying power (security).

In order to solve the foregoing problems, an information identification method according to the present invention includes: an irradiating step of irradiating, with exciting light, a light-emitting member containing a rare-earth complex; a measuring step of receiving light emitted from the light-emitting member, and of measuring spectral intensities of the light; a computing step of computing a ratio of spectral intensities at a plurality of different wavelengths among the spectral intensities thus measured; and an identifying step of identifying identification information corresponding to the ratio thus computed.

According to the foregoing arrangement, in the irradiating step, the light-emitting member containing a rare-earth complex is irradiated with exciting light. This causes the light-emitting member to emit light. In the measuring step, the light emitted from the light-emitting member is received and the spectral intensities are measured. Furthermore, in the computing step, the ratio of spectral intensities at a plurality of different wavelengths among the spectral intensities thus measured is computed. Then, in the identifying step, the identification information corresponding to the ratio thus computed is identified.

Thus, in the present invention, the rare-earth complex contained in the light-emitting member can be identified (specified) by measuring the intensities of line spectra at a plurality of different wavelengths among the light emitted from the rare-earth complex and by computing the ratio, and the identification information corresponding to the rare-earth complex is identified and authenticated. That is, since the present invention can identify the rare-earth complex contained in the light-emitting member, the present invention can provide an information identification method having an unprecedentedly high level of identifying power (security).

Further, since the present invention identifies a substance in accordance with a spectral intensity ratio, the substance can be identified even in cases where the rare-earth complex has deteriorated. There are no restrictions on use conditions such as temperature, either. Further, the rare-earth complex is transparent and colorless and therefore invisible when in a normal condition, thereby ensuring a higher level of security. Furthermore, the use of a single rare-earth ion makes it possible to recover used rare-earth ions, which are precious resources.

The information identification method according to the present invention is preferably arranged so as to include a wavelength selecting step of splitting, into spectra containing a first-wavelength line spectrum and spectra containing a second-wavelength line spectrum, the light emitted from the light-emitting member, wherein the measuring step measures intensities of the spectra that have been split by the wavelength selection section.

These line spectra at respective wavelengths are appropriately set in accordance with the emission distribution of the rare-earth complex, and are preferably any of the plurality of emission spectra. Thus, the ratio is computed in accordance with the intensities of light at two specific wavelengths. This not only makes it possible to identify the rare-earth complex, but also makes it easy to perform the computation.

The information identification method according to the present invention is preferably arranged such that the wavelength selecting step splits, by transmission, reflection, diffraction, or refraction, the light emitted from the light-emitting member.

The information identification method according to the present invention is preferably arranged such that the computing step computes a ratio between the intensity of the spectra containing the first-wavelength line spectrum and the intensity of the spectra containing the second-wavelength line spectrum among the spectral intensities thus measured.

The first-wavelength line spectrum and the second-wavelength line spectrum refer to those line spectra at specific wavelengths which are contained in the light emitted from the rare-earth complex, and to spectra of wavelengths that are measured for the purpose of computing a spectral intensity ratio.

These line spectra at respective wavelengths are appropriately set in accordance with the emission distribution of the rare-earth complex, and are preferably any of the plurality of emission spectra. Thus, the ratio is computed in accordance with the intensities of light at two specific wavelengths. This not only makes it possible to identify the rare-earth complex, but also makes it easy to perform the computation.

The information identification method according to the present invention is preferably arranged such that the first-wavelength line spectrum is a line spectrum based on magnetic dipole transition and the second-wavelength line spectrum is a line spectrum based on electric dipole transition.

The information identification method according to the present invention is preferably arranged such that: the light-emitting member contains plural types of rare-earth complex; and the computing step computes a ratio of spectral intensities at a plurality of wavelengths corresponding to each rare-earth complex.

According to the foregoing arrangement, each of the rare-earth complexes contained in the light-emitting member emits light. Moreover, the computing step computes a ratio of spectral intensities at wavelengths corresponding a spectrum emitted from each rare-earth complex. That is, although wavelengths of spectra for computing a ratio vary from one rare-earth complex to another, the computing step computes a ratio in accordance with spectral intensities at wavelengths for identifying each rare-earth complex. Therefore, even in cases where the plural types of rare-earth complex are used, each of the rare-earth complexes can be identified. This makes it possible to provide an information identification method having a higher level of identifying power (security).

In order to solve the foregoing problems, an information identification system according to the present invention includes (i) a light-emitting member containing a rare-earth complex and (ii) an information identification device for identifying identification information corresponding to the rare-earth complex, the information identification device including: a light source for irradiating, with exciting light, a light-emitting member containing a rare-earth complex; a measurement section for receiving light emitted from the light-emitting member, and for measuring spectral intensities of the light; a computation section for computing a ratio of spectral intensities at a plurality of different wavelengths among the spectral intensities thus measured; and an identification section for identifying identification information corresponding to the ratio thus computed. As with the information identification device already explained, the foregoing arrangement can provides an information identification system having an unprecedentedly high level of identifying power (security). Further, since a substance is specified (identified) in accordance with an intensity ratio of spectra, the substance can be specified even in cases where the rare-earth complex has deteriorated. There are no restrictions on use conditions such as temperature, either.

Further, the rare-earth complex is transparent and colorless and therefore invisible when in a normal state, thereby ensuring a higher level of security. Furthermore, the use of a single rare-earth ion makes it possible to recover used rare-earth ions, which are precious resources. Further, the information identification system has a simple arrangement. This makes it possible to reduce the cost of the system.

In cases where the light-emitting member contains plural types of rare-earth complex, the number of available pieces of identification information (number of pieces of information that can be encrypted) can be increased. That is, in this case, an information identification system having a vast amount of identification information can be provided.

As described in detail above, the present invention makes it possible to provide an information identification device, an information identification method, and an information identification system each of which, for the purpose of coding (arranging identification information) in accordance with the type of rare-earth complex (a rare-earth species (ion), ligands of the rare-earth complex, and the like), has a large number of available pieces of identification information (number of pieces of information that can be encrypted) and has a high level of identifying power (security). The number of available pieces of identification information (number of pieces of information that can be encrypted) can be increased by causing the light-emitting member to contain plural types of rare-earth complex.

Further, according to the present invention, the rare-earth complexes are identified by using (i) an emission spectrum based on electric dipole transition, having a wavelength unique to each rare-earth complex, whose emission intensity varies depending on the ligands of the complex and (ii) an emission spectrum based on magnetic dipole transition that does not vary depending on the ligands of the complex.

Therefore, the intensity ratio is unique to each rare-earth complex. This enables identification at a high level of identifying power (security).

Further, according to the present invention, in cases where the present invention includes a wavelength selection section, the identification of a complex, i.e., the identification of information can be processed at a high speed by measuring the intensities of spectra selected (split) by the wavelength selection section and by performing computation with use of the measured values.

The intensity ratio of spectra of the light-emitting member as measured and computed in the present invention stay constant regardless of the degree of deterioration of the rare-earth complex. Therefore, the rare-earth complex can be identified even in cases where the rare-earth complex has deteriorated. This makes it possible to provide an identifying medium that withstands long-term use. Furthermore, the intensity ratio of those spectra does not vary depending on temperature. This enables identification that is tolerant of temperature changes and stable in spite of changes in ambient temperature. Further, in cases where the light-emitting member contains a complex including one type of rare-earth ion without a mixture of rare-earth ion species, it becomes possible to easily recover the rare-earth ion.

As described above, the present invention makes it possible to realize an information identification device, an information identification method, and an information identification system each of which can prevent leakages of identification information such as IDs as required strongly by society and enables long-term use without any restrictions imposed on use conditions and without any influence of deterioration in material.

BRIEF DESCRIPTION OF THE DRAWINGS

FIG. 3 shows Embodiment 1 of the present invention, and shows a table of "LIR(Eu)", "RARE-EARTH COMPLEX", and "ID" correlated with one another.

FIG. 9 is a plan view schematically showing an arrangement of another example of an ID identification device for use in the ID identification system of FIG. 8.

Figure 1:
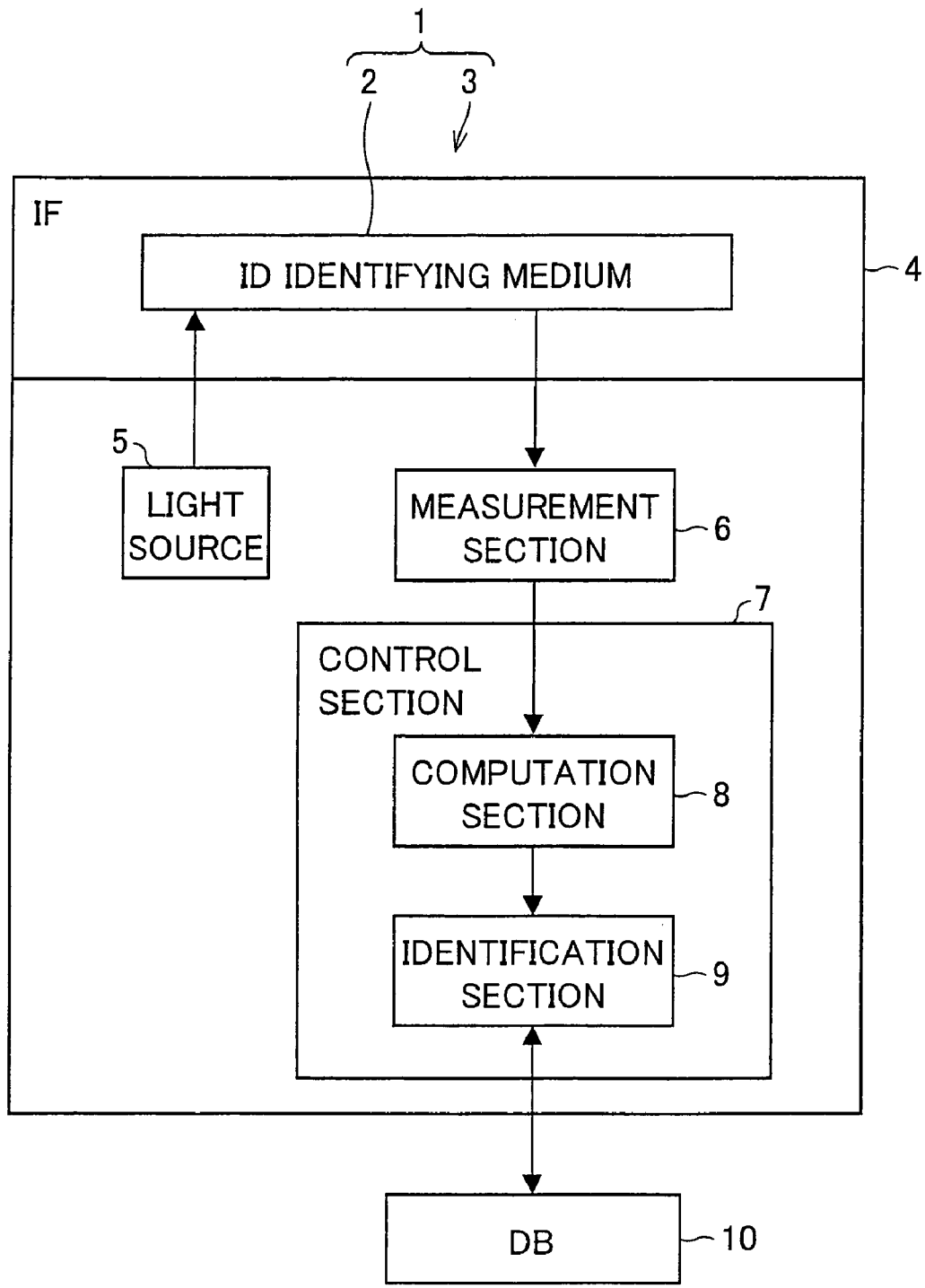
FIG. 1 shows Embodiment 1 of the present invention, and is a block diagram schematically showing an arrangement of an ID identification system.

REFERENCE NUMERALS 1, 11, 21 ID identification system (information identification system)
2, 19, 20, 22 ID identifying medium (light-emitting member)
3, 12, 23 ID identification device (information identification device)
5 Light source
6 Measurement section
8 Computation section
9 Identification section
13$a$, 13$b$, 24$a$, 24$b$ Wavelength selection section
14, 34, 44 Ultraviolet LED (light source)
15 First band-pass filter (wavelength selection section)
16 Second band-pass filter (wavelength selection section)
17 Computer (measurement section, control section)
35 Optical high pass filter (wavelength selection section)
36 Ultraviolet reflection band-pass filter (wavelength selection section)
37, 47 Separating prism (wavelength selection section)
38 Photodetector (measurement section)
39$a$, 49$a$ Substrate
39$b$, 49$b$ ID ink
41 Spectroscope (wavelength selection section)
41$a$ Diffraction grating (wavelength selection section)
41$b$ Optical Fiber
46 Ultraviolet reflection low pass filter (wavelength selection section)
48 CCD array (measurement section)

BEST MODE FOR CARRYING OUT THE INVENTION

Embodiment 1

Embodiment 1 of the present invention will be described below with reference to FIGS. 1 through 3. FIG. 1 is a block diagram schematically showing an arrangement of an ID identification system (information identification system). As shown in FIG. 1, the ID identification system of the present invention is a system that uses an ID identification device 3 to identify and authenticate an ID corresponding to identification information recorded in an ID identifying medium 2.

(ID Identifying Medium)

The ID identifying medium (light-emitting member) 2 is an information recording medium which is used for identifying an ID and in which identification information has been recorded. The ID identifying medium 2 contains a rare-earth complex, and the rare-earth complex is used as the identification information. In the present invention, the identification information recorded in the ID identifying medium 2 is identified by identifying (specifying) the rare-earth complex by measuring and computing the intensity (emission intensity) of a spectrum of light emitted from the rare-earth complex. That is, the ID identifying medium 2 of the present invention is a member to be identified for identifying identification information such as an ID. The arrangement in which the identification information is identified by using the intensity of the spectrum of the light emitted from the rare-earth complex will be fully described below.

The rare-earth complex contained in the ID identifying medium 2 is a coordinated complex having one type of rare-earth ion and plural types of ligand coordinated therearound. That is, the rare-earth complex encompasses plural types of complex having the same rare-earth ion and different combinations of ligands coordinated therearound. The present invention imposes no limitation on the type of rare-earth ion that can be used for the ID identifying medium 2, and it is possible to use any ion of all rare-earth elements.

Further, examples of the ligands for use in the rare-earth complex include bipyridine ligands, phenanthroline ligands, diketone ligands, carbamate ligands, amine ligands, and phosphine ligands. Specific examples of these ligands include compounds respectively represented by the following formulas (1) to (6):

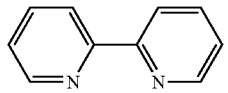

(1)

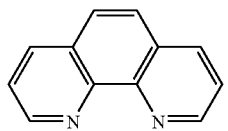

(2)

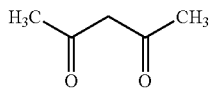

(3)

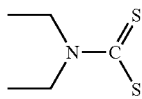

(4)

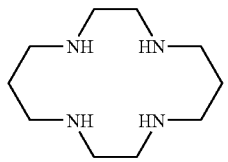

(5)

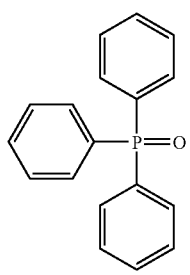

(6)

The formulas (1) to (6) represent a bipyridine compound, a phenanthroline compound, a diketone compound, a carbamate compound, an amine compound, and a phosphine compound, respectively.

However, the compounds are typical examples, and other derivatives belonging to the groups can be used. Furthermore, compounds belonging to other groups and derivatives thereof may be used. That is, the present invention imposes no limitation on the type of ligand that is used for the rare-earth complex, and it is possible to use all those ligands which can be coordinated around a rare-earth ion being used. These rare-earth complexes can be generated by using a publicly-known method.

Further, the ID identifying medium 2 is used in various shapes or forms. For example, the ID identifying medium 2 may be a card, a film, a sticker, an armband, or the like obtained by molding a resin containing the rare-earth complex. Alternatively, the ID identifying medium 2 may be an image, a figure, a character, or the like printed by using ink containing the rare-earth complex. For example, the use of the ink containing the rare-earth complex makes it possible to print an identification pattern by using an ink-jet apparatus. Further, the image, the figure, the character, or the like formed, for example, by using the ink containing the rare-earth complex may be formed into codes such as bar codes. In the form of a bar code, the number of codes is equal to the product obtained by multiplying the number of types of rare-earth complex and the number of bar codes. This makes it possible to significantly increase the number of codes. Further, the formation of an image or a figure enables two-step coding in combination with identification information thereof. This makes it possible to achieve a higher level of identifying power (security).

Furthermore, the ID identifying medium 2 is arranged so as to be identifiable by an ID identification device described below. Although the ID identification device and an ID identification method will be fully described below, the "arrangement in which the ID identifying medium is identifiable by the ID identification device" refers to the following arrangement: When the ID identifying medium 2 of the present invention is used for the ID identification device, the ID identification device can compute the intensity ratio of spectra of light emitted from the rare-earth complex contained in the ID identifying medium 2 and can, as a result of the computation, identify (specify) the rare-earth complex contained in the ID identifying medium 2, thereby identifying the identification information corresponding to the rare-earth complex.

Thus, the ID identifying medium 2 only needs to contain a rare-earth complex and to be arranged so as to be identifiable by the ID identification device. The ID identifying medium 2 is not limited in terms of its material, shape, and form. The ID identifying medium 2 may be appropriately changed in accordance with the specifications of the ID identification device described below.

(ID Identification Device)

The following describes the ID identification device (information identification device) 3 according to the present embodiment. As shown in FIG. 1, the ID identification device 3 includes an IF 4, a light source 5, a measurement section 6, and a control section 7. The present embodiment describes an example of the ID identification device 3 that is used in cases where the ID identifying medium 2 is in the form of a card. The ID identifying medium 2 is hereinafter sometimes referred to as "ID card 2".

The IF 4 is an interface for the ID card 2. When the ID card 2 is moved closer to, mounted on, or inserted into the IF 4, the IF 4 reads identification information recorded in the ID card 2. Since the ID identifying medium 2 can take various shapes or forms as well as a card from, the IF 4 is also not limited to the type which the ID identifying medium 2 is moved closer to, mounted on, or inserted into. The IF 4 can be appropriately changed in accordance with the shape and/or form of the ID identifying medium 2.

The light source 5 irradiates, with exciting light having a wavelength corresponding to the absorption wavelength of the rare-earth complex, the ID card 2 thus moved closer to, mounted on, or inserted into the IF 4. Examples of the light source 5 include light sources, such as ultraviolet LEDs, black lights, xenon lamps, short-wavelength semiconductor lasers, which can emit light in an ultraviolet region.

The measurement section 6 receives light emitted from the rare-earth complex of the ID card 2, and measures the spectral intensity (light intensity) of the light. That is, when the measurement section 6 receives the light emitted from the rare-earth complex, the measurement section 6 measures the spectral intensity and then transmits data indicative of the spectral intensity to the control section 7. The measurement section 6 may measure spectral intensities at all wavelengths or light intensities at predetermined wavelengths among the light thus received. The measurement section 6 only needs to be able to measure light intensity. Examples of the measurement section 6 include a photodiode, a photoelectron multiplier tube, a CCD, and a spectrum analyzer.

Although the present embodiment is arranged so as to include the measurement section 6 which receives the light emitted from the ID card 2 and measures the spectral intensity, the present embodiment may be arranged so as to separately include a member for receiving light emitted from the ID card 2 and a member for measuring the spectral intensity of the light thus received.

The control section 7 identifies and authenticates, in accordance with the data indicative of the spectral intensity received and measured by the measurement section 6, an ID corresponding to the identification information recorded in the ID card 2. The control section 7 includes a computation section 8 and an identification section 9.

The computation section 8 computes the ratio of spectral intensities at a plurality of predetermined wavelengths among the spectral intensity data received from the measurement section 6. For example, in cases where spectral intensities at two wavelengths are used, the computation section 8 extracts data indicative of a spectral intensity at a first wavelength and data indicative of a spectral intensity at a second wavelength from among the spectral intensity data thus received, and computes the ratio of these spectral intensities. The computation section 8 is not limited to computing the ratio of spectral intensities at two wavelengths, and may compute the ratio of spectral intensities at three or more wavelengths. Further, the computation section 8 transmits the computation result to the identification section 9.

The identification section 9 identifies and authenticates, in accordance with the computation result received from the computation section 8, the ID corresponding to the identification information recorded in the ID card 2. Upon receiving the ratio of spectral intensities as computed by the computation section 8, the identification section 9 identifies (specifies), from a database (DB) 10 in which a plurality of IDs are stored, a rare-earth complex corresponding to the ratio of spectral intensities as calculated through the computation, and identifies an ID corresponding to the rare-earth complex. With this, the ID corresponding to the identification information recorded in the ID card 2 is identified and authenticated.

In the DB 10, the ratio of spectral intensities, a rare-earth complex corresponding to the ratio, and an ID corresponding to the rare-earth complex are stored so as to correspond one-to-one with one another. That is, one rare-earth complex corresponds to one ratio, and one ID corresponds to one rare-earth complex. In the DB 10, the ratio of spectral intensities, the rare-earth complex, and the ID are stored, for example, in the form of a look-up table (LUT).

The DB 10 may be provided in the ID identification device 3, or may be provided in an external device. In cases where the DB 10 is provided in an external device, the ID identification device 3 communicates with the external device via a communication section (not shown) or the like, and identifies an ID extracted from the DB 10.

(ID Identification Method)

The following fully describes a method for identifying and authenticating an ID by using the ID identification device 3. The present embodiment describes an example where the rare-earth complex contained in the ID card 2 is a complex having a europium ion as a rare-earth ion.

When the rare-earth complex having a europium ion as a rare-earth ion is irradiated with exciting light, the rare-earth complex emits light having spectra at a plurality of wavelengths of 590 nm, 615 nm, 650 nm, and 700 nm (i.e., light having a plurality of wavelengths). This applies to all those complexes each of which has a europium ion as a rare-earth ion, regardless of combinations of ligands. However, different combinations of ligands result in variations in the intensity of the spectra (light) emitted. That is, the ratio between the spectral intensity at one wavelength and the spectral intensity at another wavelength varies from one rare-earth complex to another. That is, the ratio is a value unique to the rare-earth complex. Therefore, the rare-earth complex can be identified (specified) by calculating the ratio of spectral intensities.

In general, a rare-earth complex has a plurality of emission line spectra that include an emission line spectrum based on magnetic dipole transition and an emission line spectrum based on electric dipole transition. The emission line spectrum based on magnetic dipole transition has a light intensity unique to the rare-earth element. The emission line spectrum based on electric dipole transition has an intensity that varies depending on the type of ligand surrounding the rare-earth element, and has an intensity unique to the type of rare-earth complex. Therefore, the intensity ratio of the emission line spectrum based on electric dipole transition to the emission line spectrum based on magnetic dipole transition takes on a value unique to the rare-earth complex.

For example, in cases where the complex having a europium ion as a rare-earth ion is used, the spectrum at a wavelength of 590 nm is an emission line spectrum based on magnetic dipole transition, and is based on such transition ($\Delta J=1$) that the total number J of magnetic quantums between two levels involved in the transition varies by 1. The spectrum at a wavelength of 615 nm is an emission line spectrum based on electric dipole transition, and is based on such transition ($\Delta J=2$) that $\Delta J$ varies by 2. Thus, the rare-earth complex contained in the light-emitting member can be identified by measuring the intensities of line spectra at different wavelengths based on the two types of transition among the light emitted from the rare-earth complex and by computing the ratio.

Even when the electric dipole transition ($\Delta J=2$) is mixed with a spectrum of electric dipole transition other than $\Delta J=2$, the complex can be identified without problems by adjusting the spectral intensity ratio in identifying the complex.

The ratio of spectral intensities at any two of the four wavelengths, the ratio of spectral intensities at any three of the four wavelengths, or the ratio of spectral intensities at all of the four wavelengths may be calculated. Thus, the wavelengths for calculating the ratio of spectral intensities may be selected optionally. Further, the number of wavelengths is not limited.

In the case of magnetic dipole transition, there is no influence of an electronic field formed by the surrounding ligands, so that the wavelength and intensity of the spectrum do not vary depending on the types of ligand, i.e., the type of complex. On the other hand, in the case of electric dipole transition, the electronic field of the ligands causes a big change in the probability of transition, so that the intensity of the spectrum vary significantly depending on the type of complex whereas the wavelength of the spectrum does not vary depending on the type of complex. This makes it possible to identify the rare-earth complex by calculating the ratio of the spectral intensity of electric dipole transition to the spectral intensity of magnetic dipole transition.

In cases where a europium (Eu) ion is used, the spectral intensities at wavelengths of 590 nm and 615 nm are higher than the spectral intensities at other wavelengths, and all the complexes exhibit substantially identical spectral intensities at a wavelength of 590 nm. This shows that the selection of wavelengths of 590 nm and 615 nm makes it easy to calculate the ratio of spectral intensities and to confirm the spectral intensities. For this reason, the present embodiment calculates the ratio of spectral intensities at wavelengths of 590 nm and 615 nm.

First, a predetermined operation is performed for the light source 5 to irradiate the ID card 2 with exciting light. Then, the rare-earth complex of the ID card 2 emits light. When the measurement section 6 receives the light emitted from the rare-earth complex, the measurement section 6 measures spectral intensities. The measurement section 6 may measure spectral intensities at all the wavelengths of the light thus received, or may measure only spectra (light) at predetermined wavelengths. The measurement section 6 transmits data indicative of the spectral intensities to the computation section 8 of the control section 7.

The computation section 8 computes the ratio of the spectral intensities by using the data indicative of the spectral intensities as received from the measurement section 6. That is, in cases where the measurement section 6 has measured the spectral intensities at all the wavelengths, the computation section 8 extracts only spectral intensities at wavelengths of 590 nm and 615 nm and computes the ratio of the spectral intensities. Alternatively, in cases where the measurement section 6 has measured the spectra (light) at the predetermined wavelengths (in cases where the measurement section 6 has measured only light intensities at wavelengths of 590 nm and 615 nm), the computation section 8 computes the ratio of the light intensities in accordance with data indicative of the light intensities.

Assuming that the ratio of spectral intensities at wavelengths is LIR(Eu), the computation section calculates a value of LIR(Eu) according to the following formula:

LIR(Eu)=Spectral intensity at 615 nm/Spectral intensity at 590 nm

Then, the identification section 9 accesses the DB 10, refers to the LUT, and identifies (specifies) a rare-earth complex corresponding to the value of the ratio thus calculated. Furthermore, the identification section 9 acquires, from the LUT, an ID corresponding to the rare-earth complex thus identified (specified). This makes it possible to identify and authenticate the ID corresponding to the identification information recorded in the ID card 2.

Although the foregoing has described an example where Eu is used as a rare-earth ion, the features of magnetic dipole transition and electric transition are not limited to Eu, and apply to all the rare-earth complexes.

For example, in cases where a samarium ion (Sm(III)) is used, a similar analysis can be performed by making a comparison of intensity between magnetic dipole transition (4G5/2-5H7/2:600 nm) and electric dipole transition (4G5/2-5H9/2:650 nm) in an emission spectrum. Similarly, in cases where a terbium ion (Tb(III)) is used, identification is enabled by making a comparison between intensities at 580 nm and 545 nm in an emission spectrum. In the case of a praseodymium ion (Pr(III)), identification is enabled by making a comparison between emission intensities at 1040 nm, 490 nm, 530 nm, and 620 nm. In the case of a neodymium ion Nd(III), identification is enabled by comparing the intensity ratio of emission bands at 900 nm and the intensity ratio of emission bands at 1064 nm.

Thus, the rare-earth complex contained in the ID card 2 can be identified (specified) by calculating a value unique to the rare-earth complex. That is, the rare-earth complex can be used for the same purpose as a so-called "fingerprint". This makes it possible to use a rare-earth complex for identification and authentication of an ID by correlating the rare-earth complex with the ID in advance.

The following provides a more specific explanation by exemplifying cases where the five complexes represented by the formulas (7) to (11) are used as rare-earth complexes, respectively.

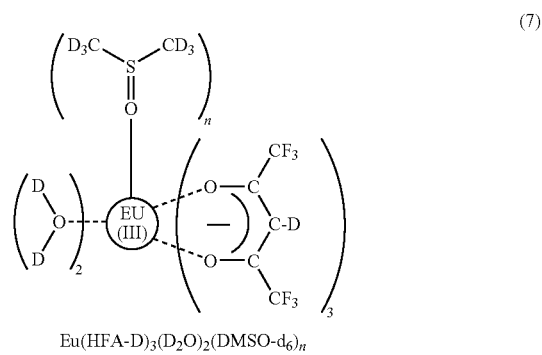

Eu(HFA-D)$_3$(D$_2$O)$_2$(DMSO-d$_6$)$_n$ (7)

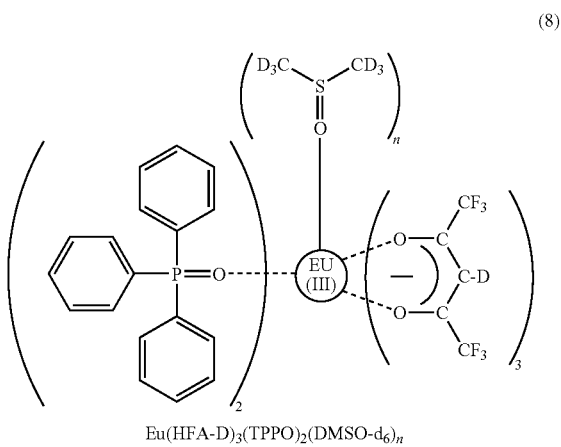

Eu(HFA-D)$_3$(TPPO)$_2$(DMSO-d$_6$)$_n$ (8)

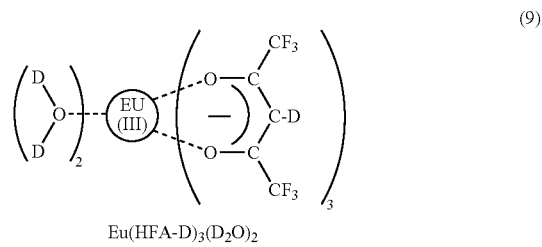

Eu(HFA-D)$_3$(D$_2$O)$_2$ (9)

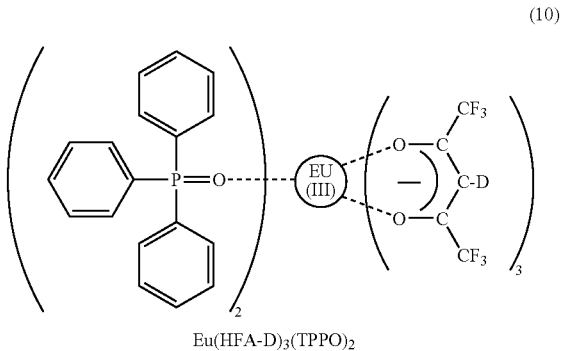

Eu(HFA-D)$_3$(TPPO)$_2$ (10)

-continued

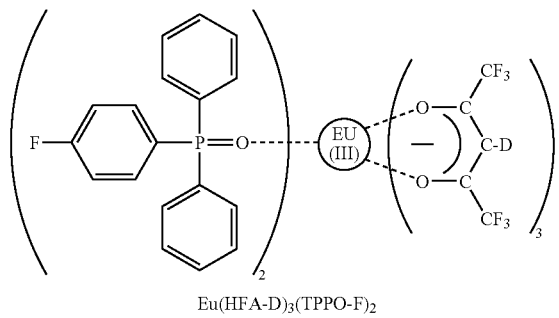

$Eu(HFA-D)_3(TPPO-F)_2$ (11)

Figure 2:
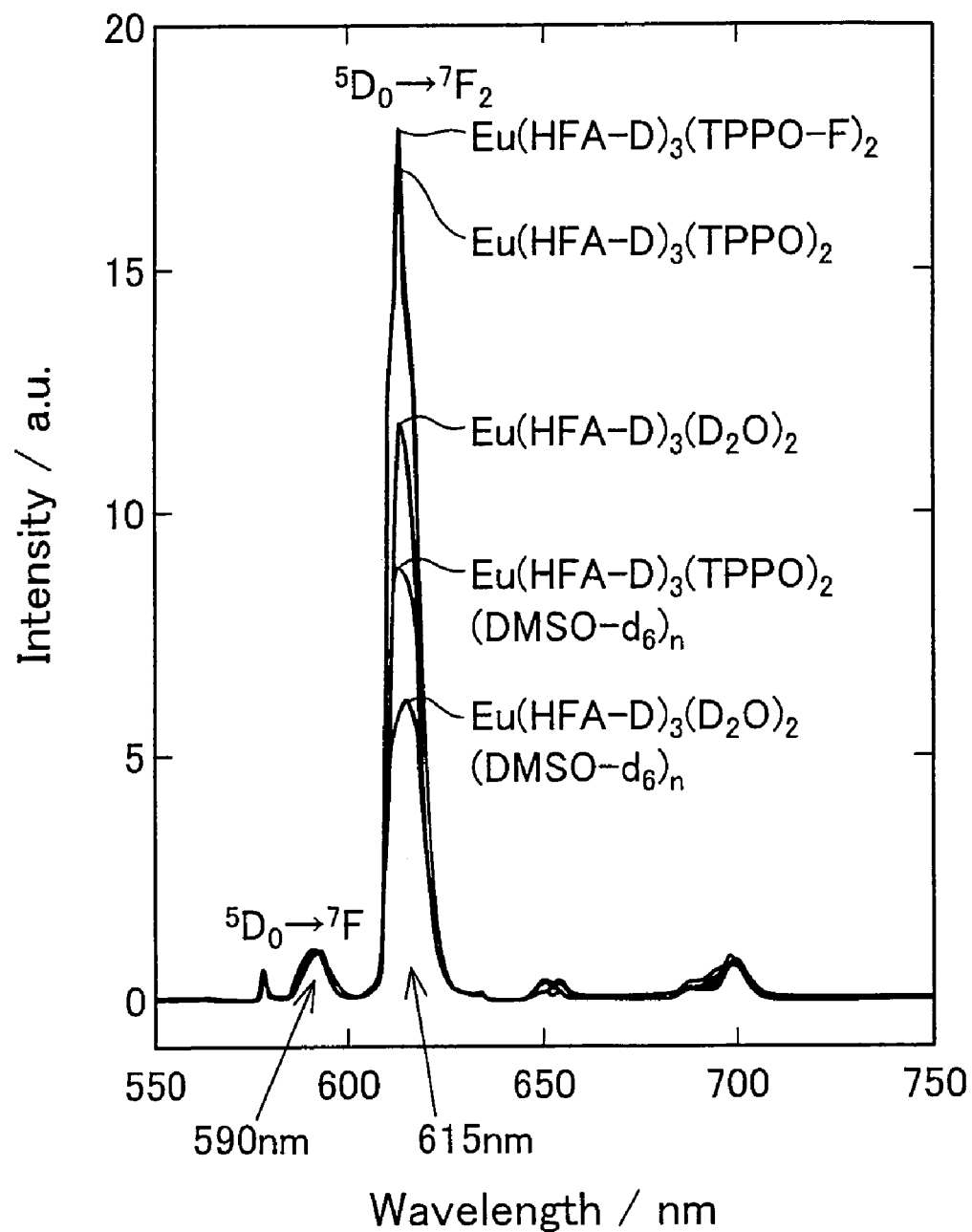
FIG. 2 shows Embodiment 1 of the present invention, and shows the emission spectra of rare-earth complexes.

FIG. 2 shows the emission spectra of the complexes represented by the formulas (7) to (11), respectively. FIG. 2 is standardized so that the emission spectrum (emission peak) of each of the complexes at 590 nm is 1. As shown in FIG. 2, when the spectral intensities (emission peaks, emission line spectra) at 590 nm are equalized, all the complexes exhibit different spectral intensities at 615 nm. That is, the value of a ratio calculated from the value of spectral intensity at 590 nm and the value of spectral intensity at 615 nm varies among the complexes.

The computation section of the ID identification device calculates LIR(Eu) by using the spectral intensities thus measured. As shown in FIG. 2, LIR(Eu)=6 in the case of $Eu(HFA-D)_3(D_2O)_2(DMSO-d_6)_n$ represented by the formula (7), and LIR(Eu)=8 in the case of $Eu(HFA-D)_3(TPPO)_2(DMSO-d_6)_n$ represented by the formula (8). Similarly, LIR(Eu)=12 in the case of $Eu(HFA-D)_3(D_2O)_2$ represented by the formula (9), and LIR(Eu)=17 in the case of $Eu(HFA-D)_3(TPPO)_2$ represented by the formula (10), and LIR(Eu)=18 in the case of $Eu(HFA-D)_3(TPPO-F)_2$ represented by the formula (II).

Further, FIG. 3 shows the LUT stored in the DB. As shown in FIG. 3, the LUT is a table in which LIR(Eu), a rare-earth complex, and an ID are correlated with one another. The identification section accesses the DB, refers to the LUT, and identifies (specifies) the rare-earth complex corresponding to the LIR(Eu). Then, the identification section acquires ID data corresponding to the rare-earth complex thus identified (specified), and identifies and authenticates the ID.

For example, in cases where LIR(Eu) is 6, the identification section identifies (specifies), as "$Eu(HFA-D)_3(D_2O)_2(DMSO-d_6)_n$", the rare-earth complex contained in the ID card, and acquires an ID "A" corresponding to the rare-earth complex. Thus, the identification section can identify and authenticate, as "A", the ID corresponding to the identification information recorded in the ID card used for identification. Also in the case of the other rare-earth complexes having different LIR(Eu), IDs can be similarly identified and authenticated.

In the case of a rare-earth complex known in advance, the rare-earth complex can be identified (specified) by using only the value of a ratio of spectral intensities. On the other hand, in the case of a rare-earth complex unknown in advance, the rare-earth metal cannot be identified (specified) by using only the value of a ratio of spectral intensities, but can be identified (specified) by using the wavelengths at which the spectral intensities were measured and the ratio of the spectral intensities.

Further, in the present embodiment, a period of approximately one second will suffice to irradiate the ID identifying medium with exciting light. Further, assuming that the ID is identified approximately 10 times per day, the ID identifying medium is irradiated with exciting light for approximately 10 seconds per day. That is, the ID identifying medium is irradiated with exciting light for approximately 3,650 seconds (one hour) per year. Even when the ID identifying medium is irradiated with exciting light for approximately 10 hours, the rare-earth complex will not deteriorate. Therefore, even in cases where the ID identification system is used for 10 year or longer, the rare-earth complex of the ID identifying medium will not deteriorate. This enables long-term use.

Furthermore, the present embodiment uses a complex having one type of rare-earth ion and plural types of ligand coordinated therearound. For this reason, even in cases where the rare-earth complex has deteriorated, the ID identification device neither fails to normally identify an ID nor malfunctions, because the ID identification device is arranged so as to compute the ratio of spectral intensities.

(Uses of the Id Identification System)

As described above, the emission spectrum of a rare-earth complex is a spectrum that has peaks in a plurality of wavelength regions, and the height ratio of the peaks (i.e., spectral intensity ratio) is a value unique to the rare-earth complex. The present invention considers the spectrum intensity ratio as a so-called "fingerprint of the substance", prepares an ID identifying medium in which the "fingerprint of the substance" is correlated with personal information, and builds an ID identification system capable of identifying and authenticating the personal information by reading the "fingerprint of the substance".

The ID identification system is arranged so as to read the "fingerprint of the substance" (identify (specify) the rare-earth complex) by calculating the ratio of spectral intensities at specific wavelengths, and therefore functions normally even in cases where the rare-earth complex has deteriorated due to light or heat. Further, the ID identification system is not limited in operating temperature or the like. For this reason, the ID identification system of the present invention is a high-precision ID identification and authentication system, and the use of the ID identification system makes it possible to build an advanced identification and authentication security system.

Therefore, the ID identification system can be used, for example, for controlling entering and leaving of guests into and from hotels and of members into and from exclusive clubs, for security locks for use in houses and apartment buildings, and for security systems for protecting information management systems through connections to personal computers at companies.

Embodiment 2

Embodiment 2 of the present invention will be described with reference to FIGS. 4 and 5. For convenience of explanation, members having the same functions as those described in Embodiment 1 are given the same referential numerals, and will not be described below.

The present embodiment is different from Embodiment 1 in terms of ID identification devices and identical to Embodiment 1 in terms of the other arrangements. For this reason, the present embodiment mainly describes an arrangement of an ID identification device. Further, the present embodiment can use the same ID identifying medium (light-emitting member) as Embodiment 1.

(ID Identification Device)

Figure 4:
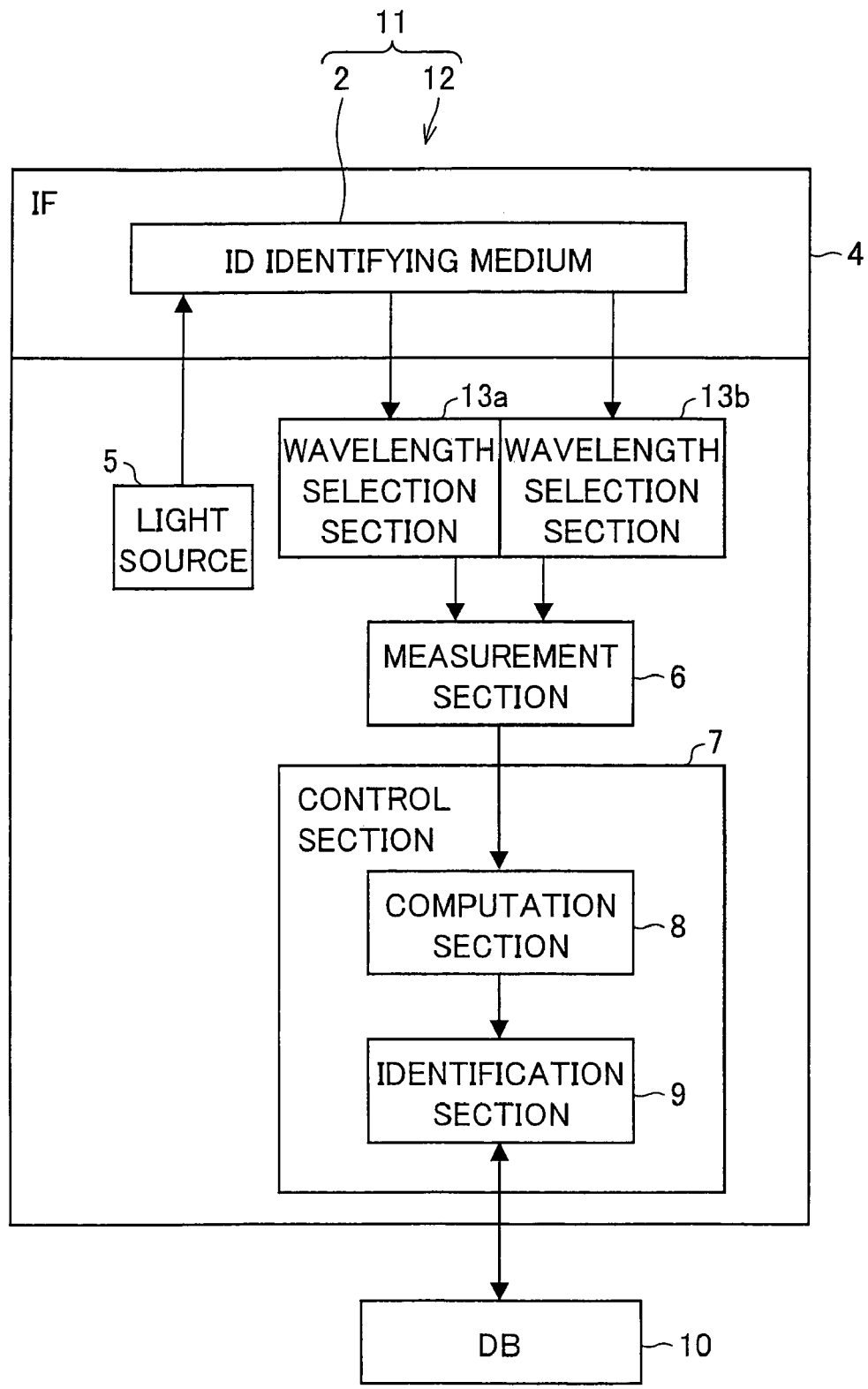
FIG. 4 shows Embodiment 2 of the present invention, and is a block diagram schematically showing an arrangement of an ID identification system.

FIG. 4 is a block diagram schematically showing an arrangement of an ID identification system 11 according to the present embodiment. The ID identification system (information identification system) 11 is a system that uses an ID identification device 12 to identify and authenticate an ID corresponding to identification information recorded in an ID identifying medium 2.

As shown in FIG. 4, the ID identification device (information identification device) 12 includes an IF 4, a light source 5, wavelength selection sections 13a and 13b, a measurement section 6, and a control section 7. As with the Embodiment 1, the ID identification device 12 according to the present embodiment uses an ID identifying medium 2 that is in the form of a card (ID card). The ID identifying medium 2 is hereinafter sometimes referred to as "ID card 2".

The wavelength selection sections 13a and 13b transmit light (spectra) at specific wavelengths, respectively. The wavelength selection sections 13a and 13b are provided in such locations that light emitted from the ID card 2 travels through the wavelength selection sections 13a and 13b before reaching the measurement section 6. That is, the light emitted from the ID card 2 reaches the measurement section 6 after traveling through the wavelength selection sections 13a and 13b. Accordingly, the measurement section 6 of the present embodiment receives only light (spectra) at specific wavelengths. The wavelength selection sections 13a and 13b only need to selectively transmit specific wavelengths. Examples of the wavelength selection sections 13a and 13b include band-pass filters.

For example, by using an optical pass filter, an optical low pass filter, or an optical high pass filter as the wavelength selection sections 13a and 13b to split spectra of a plurality of complexes including one type of rare-earth ion, the spectra can be split into a spectrum of magnetic dipole transition ($\Delta J=1$) and a spectrum of electric dipole transition. With this, the ID identification device can be arranged such that the measurement section 6 measures the spectrum of magnetic dipole transition ($\Delta J=1$) and the main spectrum of electric dipole transition ($\Delta J=2$) and that the computation section 8 computes the ratio of intensities thereof.

The term "optical pass filter" here means a filter that transmits only a given wavelength. The term "optical low pass filter" here means a filter that passes wavelengths longer than a predetermined wavelength and reflects wavelengths shorter than the predetermined wavelength. The term "optical high pass filter" here means a filter that transmits wavelengths shorter than a predetermined wavelength and reflects wavelengths longer than the predetermined wavelength.

Especially in cases where optical low pass filters including dielectric multilayer films are used as the wavelength selection sections 13a and 13b to split the spectra into two, the sole object is to identify a complex including one type of rare-earth ion. In cases where a plurality of rare-earth complexes including different rare-earth ions are identified, the present embodiment can be used if the rare-earth complexes are positionally separated from one another as in a bar code.

The "light (spectra) at specific wavelengths" refers to light (spectra) at wavelengths that are used for calculating a ratio of spectral intensities to identify (specify) a rare-earth complex contained in the ID card 2. That is, the measurement section 6 receives only light (spectra) at wavelengths that are used for calculating the ratio of spectral intensities. Therefore, in cases where the ID card 2 contains a rare-earth complex known in advance, it is only necessary to use wavelength selection sections 13a and 13b corresponding to the rare-earth complex. That is, in order to calculate a ratio of spectral intensities at two wavelengths, it is only necessary to use wavelength selection sections 13a and 13b that transmit light (spectra) at the respective wavelengths.

For this reason, the measurement section 6 measures only spectral intensities at wavelengths necessary for calculating a ratio of spectral intensities, and does not need to measure spectral intensities at all wavelengths. Further, since the measurement section 6 preliminarily measures only spectral intensities at wavelengths that are used for calculating a ratio of spectral intensities, the computation section 8 can perform computation by directly using data indicative of the spectral intensities as received from the measurement section 6. That is, since there is no need to select spectral intensities at specific wavelengths, the computation is facilitated and the speed of processing is increased.

(ID Identification Method)

The following fully describes a method for identifying and authenticating an ID by using the ID identification device 12. As with Embodiment 1, the present embodiment describes an example where a complex having a europium ion as a rare-earth ion is used. Further, the spectral intensities at wavelengths of 590 nm and 615 nm are measured, and the ratio of the spectral intensities is calculated. However, the selection of wavelengths may be optional. FIG. 5 schematically shows a more specific arrangement of the ID identification device 12, and the following description is based on FIG. 5.

The ID identification device 12 includes: ultraviolet LEDs 14 (light source 5); a first band-pass filter (BPF) 15 (wavelength selection section 13a), which transmits only light (spectrum) at a wavelength of 590 nm; a second band-pass filter 16 (wavelength selection section 13b), which transmits only light (spectrum) at a wavelength of 615 nm; a computer 17 (measurement section 6 and control section 7), and photodetectors 18 (not shown in FIG. 4).

Figure 5:
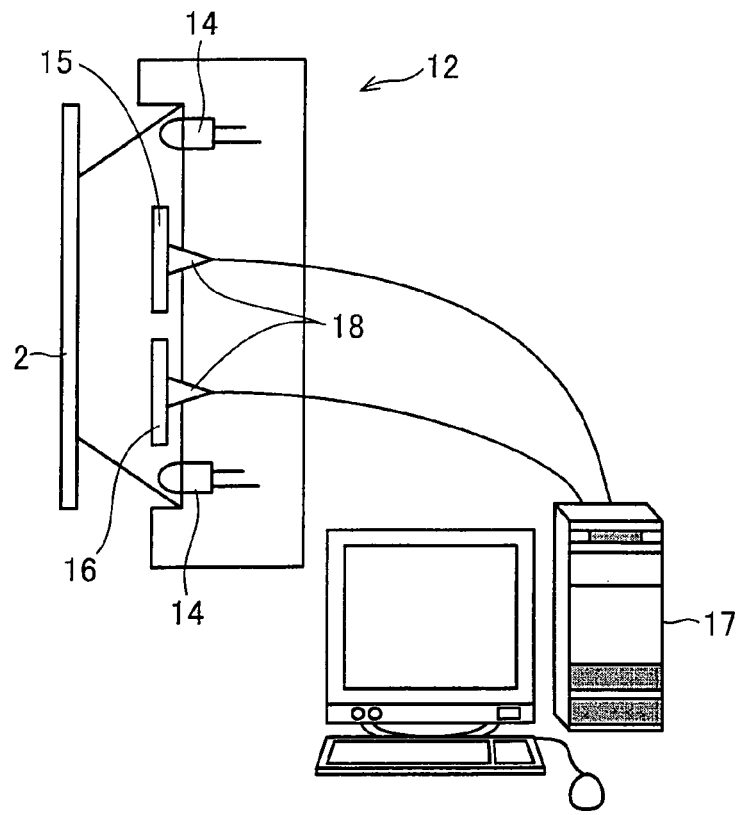
FIG. 5 shows Embodiment 2 of the present invention, and schematically shows a more specific arrangement of an ID identification device.

As shown in FIG. 5, when the ultraviolet LEDs 14 irradiate the ID card 2 with ultraviolet rays (exciting light), the rare-earth complex of the ID card 2 emits light. Among the light emitted from the rare-earth complex, light (spectrum) at a wavelength of 590 nm and light (spectrum) at a wavelength of 615 nm are passed through the first and second band-pass filters, respectively, detected by the photodetectors 18, and then transmitted to the computer 17. In the computer 17, the measurement section 6 measures spectral intensities at those wavelengths, and transmits, to the computation section 8 of the control section 7, data indicative of the spectral intensities thus measured.

The computation section 8 computes the ratio of the spectral intensities by using the data indicative of the spectral intensities as received from the measurement section 6. That is, assuming that the ratio of the spectral intensities is LIR (Eu), the computation section calculates the value of LIR(Eu) according to the following formula:

LIR(Eu)=Spectral intensity at 615 nm/Spectral intensity at 590 nm

Then, the identification section 9 accesses the DB 10, refers to the LUT, and identifies (specifies) a rare-earth complex corresponding to the value of the ratio thus calculated. Furthermore, the identification section 9 acquires, from the LUT, an ID corresponding to the rare-earth complex thus specified. This makes it possible to identify and authenticate the ID corresponding to the identification information recorded in the ID card 2.

Thus, the rare-earth complex contained in the ID card 2 can be identified (specified) by calculating a value unique to the rare-earth complex. That is, the rare-earth complex can be used for the same purpose as a so-called "fingerprint". This makes it possible to use a rare-earth complex for identification and authentication of an ID by correlating the rare-earth complex with the ID in advance.

Even in cases where other specific examples of ID identification and authentication and other rare-earth complexes are used, it is possible to identify and authenticate an ID in the same manner as in Embodiment 1.

Since the present embodiment uses one type of rare-earth ion known in advance, it is possible to identify (specify) the rare-earth complex by using only the value of the ratio of spectral intensities. However, the rare-earth complex may be identified (specified) in accordance with both the wavelengths at which the spectral intensities are measured and the ratio of the spectral intensities.

Further, as with Embodiment 1, the present embodiment can be used as an advanced ID identification system.

In the present embodiment, the provision of wavelength selection sections makes it possible to determine wavelengths for computing an intensity ratio of line spectra. This makes it only necessary for the wavelength selection sections to select (split) spectra containing line spectra at predetermined wavelengths and for the measurement section to measure the intensities of the line spectra at the respective wavelengths. This makes it possible to increase the speed of processing, and to provide an information identification device having a higher level of identifying power (security).

Embodiment 3

Embodiment 3 of the present invention will be described with reference to FIGS. 6 through 10. For convenience of explanation, members having the same functions as those described in Embodiment 1 are given the same referential numerals, and will not be described below.

(ID Identifying Medium)

An identifying medium (light-emitting member) according to the present embodiment contains plural types of rare-earth complex. The plural types of rare-earth complex may be a plurality of complexes including identical rare-earth ions, may be a plurality of rare-earth complexes including different rare-earth ions, or may be a mixture of both. However, in order to precisely measure the spectral intensity of light emitted from each of the rare-earth complexes, it is preferable that a plurality of complexes including totally different rare-earth ions be used. Therefore, the present embodiment exemplifies an ID identifying medium manufactured with use of a plurality of complexes including totally different rare-earth ions.

The rare-earth complexes of the present embodiment can be the same rare-earth complexes as in Embodiment 1. Further, the ID identifying medium can be of the same material, shape, and/or form as in Embodiment 1. The ID identifying medium can be appropriately changed in accordance with the specifications of an ID identification device described later.

For example, in cases where the ID identifying medium is manufactured by molding a resin containing plural types of rare-earth complex, the ID identifying medium can be manufactured by molding the resin containing all the rare-earth complexes. In this case, a mixture of the rare-earth complexes exists in every region of the ID identifying medium.

Meanwhile, the ID identifying medium can be manufactured in a different way. For example, the ID identifying medium can be manufactured by separately molding resins each containing a single rare-earth complex and by combining the resins thus molded. In this case, the rare-earth complexes are not mixed, so that the ID identification medium has a plurality of regions in each of which a single rare-earth complex exists. Such an arrangement makes it possible to recover used rare-earth ions, which are precious resources.

Figure 6:
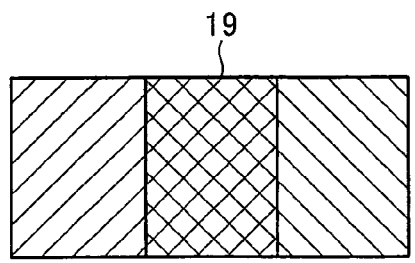
FIG. 6 shows Embodiment 3 of the present invention, and shows an example of an ID identifying medium.
Figure 7:
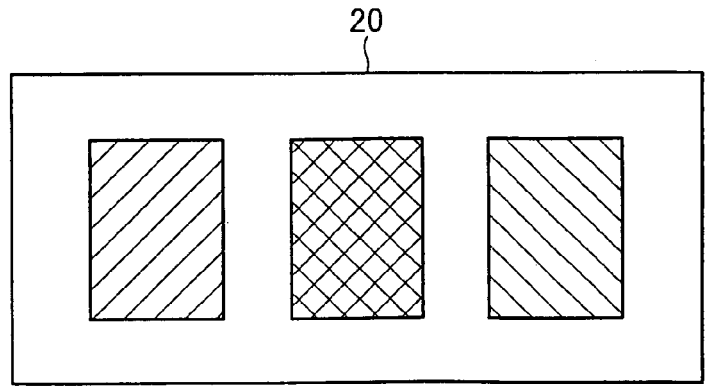
FIG. 7 shows Embodiment 3 of the present invention, and shows an example of an ID identifying medium.

FIGS. 6 and 7 show examples of such an ID identifying medium. As shown in FIG. 6, in cases where the ID identifying medium 19 is an ID card, the ID identifying medium having a plurality of regions in which different rare-earth complexes exist can be manufactured by joining molded articles respectively made of resins each containing a single rare-earth complex. Alternatively, as shown in FIG. 7, the ID identifying medium 20 can be similarly manufactured by pasting, in predetermined positions, films or stickers each containing a single rare-earth complex.

Moreover, in any one of the above cases, the identification information recorded in the ID identifying medium is identified by measuring and computing the spectral intensity (emission intensity) of light emitted from each of the rare-earth complexes. It should be noted that the ID identifying medium is not limited to these arrangements.

(ID Identification Device)

Figure 8:
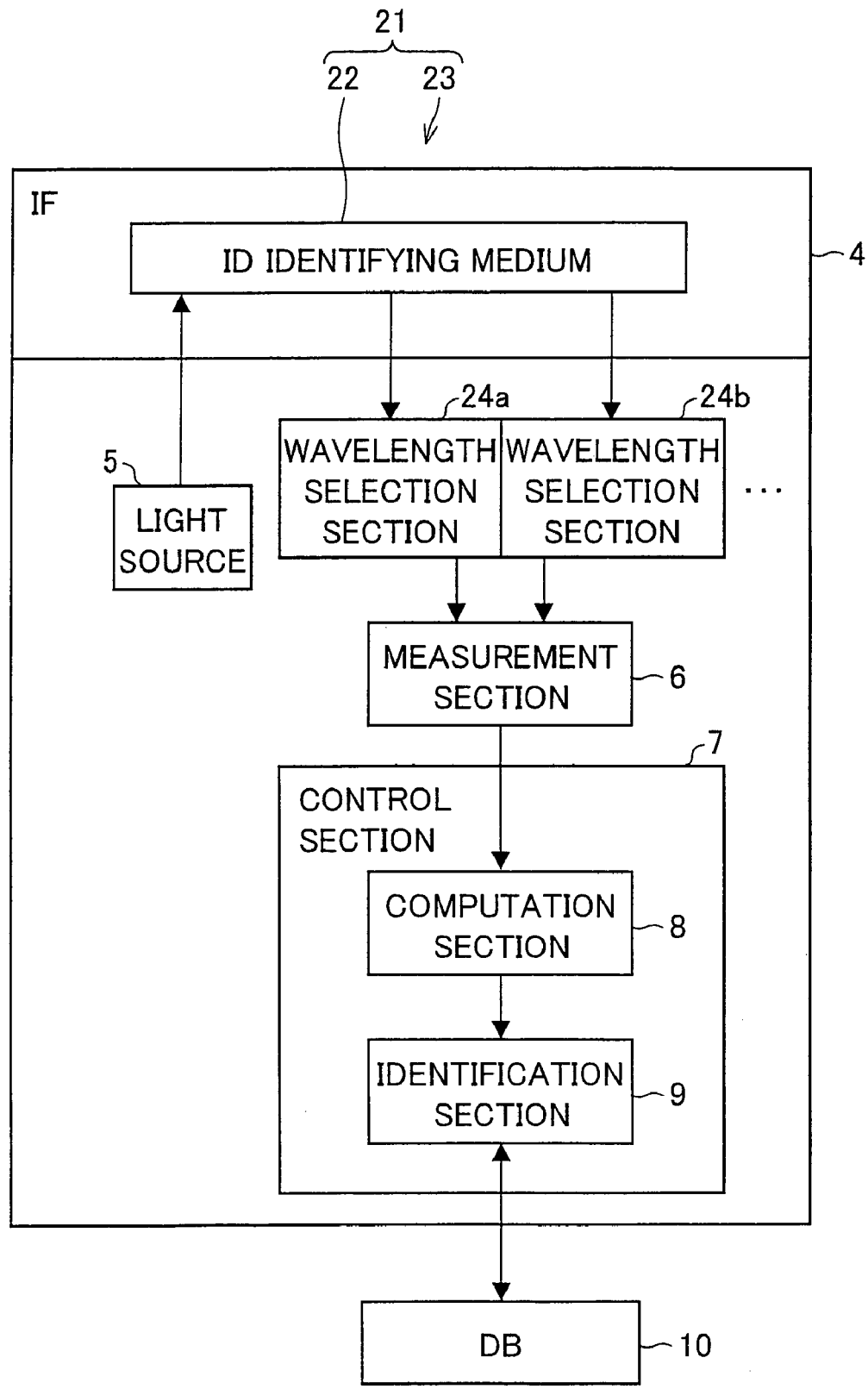
FIG. 8 shows Embodiment 3 of the present invention, and is a block diagram schematically showing an arrangement of an ID identification system.

FIG. 8 is a block diagram schematically showing an arrangement of an ID identification system 21 according to the present embodiment. As shown in FIG. 8, the ID identification device 21 uses an ID identification device 23 to identify and authenticate an ID corresponding to identification information recorded in an ID identifying medium 22.

The ID identification device (information identification device) 23 includes an IF 4, a light source 5, wavelength selection sections 24*a*, 24*b*, and . . . , a measurement section 6, and a control section 7. Examples of the ID identifying medium 22 include the aforementioned ID identifying media 19 and 20. The present embodiment assumes that the ID identification device 23 is used for the ID identifying medium 19. The ID identifying medium 19 is hereinafter sometimes referred to as "ID card 19".

The wavelength selection sections 24*a*, 24*b*, and . . . transmit light (spectra) at specific wavelengths, respectively. The wavelength selection sections 24*a*, 24*b*, and . . . are provided in such locations that light emitted from the ID card 19 travels through the wavelength selection sections 24*a*, 24*b*, and . . . before reaching the measurement section 6. That is, the light emitted from the ID card 19 reaches the measurement section 6 after traveling through the wavelength selection sections 24*a*, 24*b*, and . . . . Accordingly, the measurement section 6 of the present embodiment receives only light (spectra) at specific wavelengths. The wavelength selection sections 24*a*, 24*b*, and . . . only need to selectively transmit specific wavelengths. Examples of the wavelength selection sections 24*a*, 24*b*, and . . . include band-pass filters.

The "light (spectra) at specific wavelengths" refers to light (spectra) at wavelengths that are used for calculating a ratio of spectral intensities among the light emitted from a rare-earth complex contained in the ID card 19. That is, the measurement section 6 receives only the light (spectra) at wavelengths that are used for calculating the ratio of spectral intensities.

Incidentally, in cases where the ID identifying medium contains plural types of rare-earth complex, it is necessary to measure and compute the intensities of spectra (light) respectively emitted from the rare-earth complexes. Further, in order to measure spectral intensities of one type of rare-earth ion at two wavelengths, two wavelength selection sections are needed. That is, the ID identification device 23 has 2n wavelength selection sections in cases where n types of rare-earth ion are used (n being an integer of not less than 2). In cases where the ID card 19 contains three types of rare-earth complex as in the present embodiment, the ID identification device 23 only needs to be arranged so as to have six wavelength selection sections.

The light having traveled through the wavelength selection sections 24*a*, 24*b*, and . . . reaches the measurement section 6, and the measurement section 6 measures the intensity of each spectrum (light). The computation section 8 uses, among data indicative of the spectral intensities measured by the measurement section 6, data indicative of spectral intensities at a pair of wavelengths corresponding to each rare-earth complex, and computes the ratio of the spectral intensities. Moreover, the identification section 9 identifies and authenticates an ID in accordance with the ratio of the spectral intensities of light emitted from each rare-earth complex.

In the present embodiment, the ID identification device is not limited to this arrangement. For example, the ID identification device can be arranged so as not to include the wavelength selection sections 24*a*, 24*b*, and . . . . In this case, it is only necessary that the measurement section 6 be set to measure spectral intensities at all wavelengths and the computation section 8 be set to extract data indicative of spectral intensities at predetermined wavelengths from data indicative of the spectral intensities at all wavelengths and to compute a spectral intensity ratio.

For example, the ID identification device according to the present embodiment can be arranged so as to be combined with circularly-polarized light detection. That is, the ID identification device can be arranged so as to include, in addition to a mechanism for identifying information by calculating the intensity ratio of emission spectra at different wavelengths of a rare-earth complex contained in a light-emitting member and by identifying the rare-earth complex, a mechanism for identifying circularly-polarized light information of the rare-earth complex contained in the light-emitting member. Some rare-earth complexes are optically anisotropic, and such rare-earth complexes exhibit circularly-polarized fluorescence spectra. Therefore, more highly confidential coding can be performed by performing circular polarization with use of an optically anisotropic complex and by performing coding with use of a spectral intensity ratio.

Furthermore, another example of the arrangement of the ID identification device is an ID identification device that identifies a plurality of complexes including two or more types of rare-earth ion. FIG. 9 is a plan view schematically showing an arrangement of another example of the ID identification device according to the present embodiment. In cases where spectra of a plurality of complexes including two or more types of rare-earth ion are split, it is not sufficient to split the spectra into two by the optical low pass filter or the optical high pass filter. The spectroscopic function needs to be further improved. The ID identification device of FIG. 9 is arranged to use an ID card or the like obtained by applying ID ink (ink containing a rare-earth complex) 39*b* onto a substrate (ID card substrate) 39*a*, and to read data included in the ID card or the like inserted in the direction of the arrow of FIG. 9 (i.e., the direction in which the ID card or the like is inserted or the reading direction).

Such an ID identification device is preferably arranged such that, instead of an optical high pass filter 35 including a dielectric multiplayer film, a transmissive optical band-pass filter 36 of FIG. 9 is used for reflecting exciting ultraviolet light in a separating prism (spectroscopic prism) 37. That is, the optical band-pass filter 36 has such a bandwidth as to reflect ultraviolet light and pass a magnetic dipole transition spectrum and a main electric dipole transition spectrum emitted from each rare-earth complex. Thus, even in cases where a plurality of rare-earth ions are mixed, the rare-earth complexes can be identified by combining a plurality of band-pass filters, optical low pass filters, and optical high pass filters in accordance with spectra of the rare-earth ions, respectively.

Figure 10:
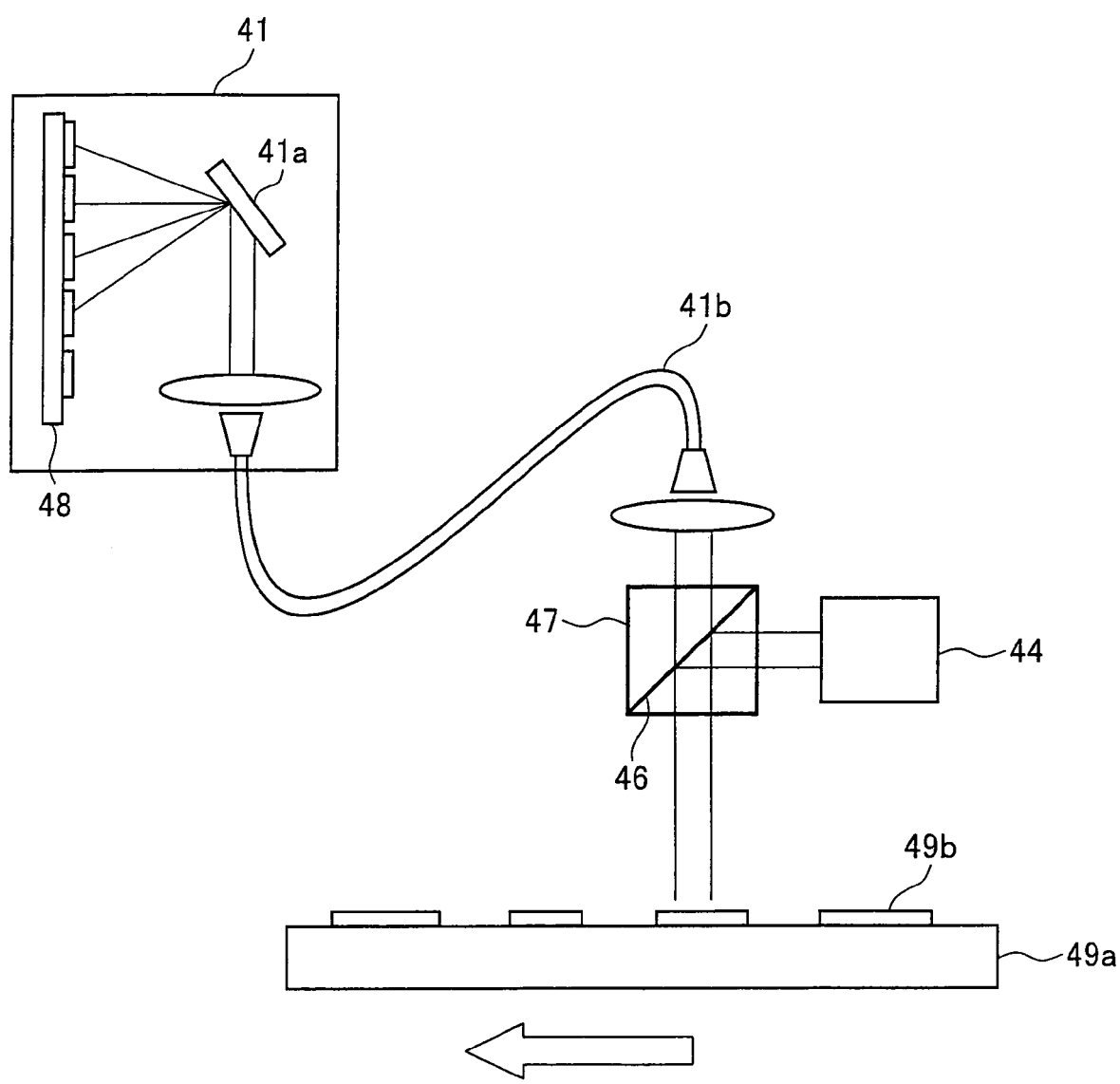
FIG. 10 is a plan view schematically showing an arrangement of still another example of an ID identification device for use in the ID identification system of FIG. 8.

Furthermore, the ID identification device that identifies a plurality of complexes including two or more types of rare-earth ion can be arranged so as to use a spectroscope including a diffraction grating. FIG. 10 is a plan view schematically showing an arrangement of still another example of the ID identification device according to the present embodiment. In the ID identification device of FIG. 10, after fluorescence spectrum light and reflected ultraviolet light are split from each other by an optical low pass filter 46 of a separating prism 47, the fluorescence spectrum light is guided via an optical fiber 41*b* to a spectroscope 41 including a diffraction grating 41*a*. Then, beams of spectrum light split by the diffraction grating 41*a* enter a one-dimensional CCD array 48, and the spectral intensities of the beams of spectrum light are measured. Such an arrangement makes it possible to obtain the intensity ratio of spectra corresponding to each rare-earth complex, thereby identifying a complex of a plurality of rare-earth ions. As with the ID identification device of FIG. 9, the ID identification device of FIG. 10 is arranged to use an ID card or the like obtained by applying ID ink (ink containing a rare-earth complex) 49*b* onto a substrate (ID card substrate) 49*a*, and to read data included in the ID card or the like inserted in the direction of the arrow of FIG. 10 (i.e., the direction in which the ID card or the like is inserted or the reading direction).

(ID Identification Method)

The following describes a method for identifying and authenticating an ID according to the present embodiment. The present embodiment uses a plurality of rare-earth complexes, and identifies and authenticates an ID by calculating the spectral intensity ratio of beams of light respectively emitted from the rare-earth complexes.

Specifically, a spectral intensity ratio is calculated for each rare-earth complex contained in the ID identifying medium 22, and the rare-earth complex is identified (specified) in accordance with the spectral intensity ratio and the wavelengths at which the spectral intensity ratio was calculated. Then, the ID is identified and authenticated by acquiring an ID corresponding to a combination of the rare-earth complexes thus identified (specified).

The following describes an example where the three types of rare-earth complex contained in the ID card 19 are a complex containing a europium ion, a complex containing a terbium ion, and a complex containing a neodymium ion.

As for light emitted from the europium-ion-containing rare-earth complex, the spectral intensities of the light at wavelengths of 590 nm and 615 nm are measured, and the ratio of the spectral intensities is computed. As for light emitted from the terbium-ion-containing rare-earth complex, the spectral intensities of the light at wavelengths of 487 nm and 545 nm are measured, and the ratio of the spectral intensities is computed. As for light emitted from the neodymium-ion-containing rare-earth complex, the spectral intensities of the light at wavelengths of 885 nm and 1054 nm are measured, and the ratio of the spectral intensities is computed.

When the measurement section 6 receives beams of light respectively emitted from the rare-earth complexes contained in the ID card 19, the measurement section 6 measures spectral intensities at wavelengths respectively corresponding to the rare-earth complexes, and transmits data indicative of the spectral intensities to the control section 7. In the control section 7, the computation section 8 extracts data indicative of a pair of spectral intensities from the data indicative of the spectral intensities as received from the measurement section 6, and computes the ratio of the pair of spectral intensities.

For example, assuming that the ratio of the spectral intensities of the light emitted from the europium-ion-containing rare-earth complex is LIR(Eu), that the ratio of the spectral intensities of the light emitted from the terbium-ion-containing rare-earth complex is LIR(Tb), and that the ratio of the spectral intensities of the light emitted from the neodymiumion-containing rare-earth complex is LIR(Nd), the computation section calculates the respective values of LIR(Eu), LIR(Tb), and LIR(Nd) according to the following formulas:

LIR(Eu)=Spectral intensity at 615 nm/Spectral intensity at 590 nm

LIR(Tb)=Spectral intensity at 487 nm/Spectral intensity at 545 nm

LIR(Nd)=Spectral intensity at 885 nm/Spectral intensity at 1054 nm

The identification section 9 accesses the DB 10, refers to the LUT, and identifies (specifies) a combination of rare-earth complexes that corresponds to the values of the ratios thus calculated. Furthermore, the identification section 9 acquires, from the LUT, an ID corresponding to the combination of rare-earth complexes thus identified (specified). This makes it possible to identify and authenticate the ID corresponding to the identification information recorded in the ID card 19.

Thus, the rare-earth complexes are used for the same purpose as a so-called "fingerprint", and a combination of the rare-earth complexes can be used for identification and authentication of an ID by correlating the combination of the rare-earth complexes with the ID in advance. Further, even in cases where specific examples of ID identification and other rare-earth complexes are used, it is possible to identify and authenticate an ID in the same manner as in Embodiment 1.

(Uses of the Id Identification System)

Further, as with Embodiment 1, the present embodiment can be used as an advanced ID identification system. Furthermore, since the present embodiment uses plural types of rare-earth complex, the present embodiment can use a larger number of IDs (combinations of codes) than in a case where a single rare-earth complex is used.

For example, there exist several tens of representative types of ligand capable of being coordinated around a rare-earth ion, and there exist 10 or more types of derivative of each of the types of ligand. Therefore, there exist 1,000 or more types of complex with respect to a single rare-earth ion. Furthermore, in cases where three types of rare-earth ion are used, even a simple model has 1,000,000,000 or more patterns of combinations. This makes it possible to employ 1,000,000,000 or more IDs (combinations of codes). Therefore, the ID identification system can be used without problems as a security system that requires a huge number of IDs.

Further, in the case of such ID identifying media 19 and 20 as shown in FIGS. 8 and 9, the rare-earth complexes are not mixed and exist in separate regions. Therefore, even when plural types of rare-earth complex are used, the rare-earth ions can be recycled.

Example of Experiment to Cause a Resin to Contain a Europium Complex

The following describes an example of experiment to cause a resin to contain a europium complex. In the present invention, examples of a method for causing a resin to contain a rare-earth complex include a "spin coat method", a "casting method", and a "thermal molding processing method" in addition to a method described below, and are not limited to the following example of experiment.

A europium complex (europium ion concentration: 0.7 wt %) and a polymerization initiator (AIBN: 0.05 wt %) were dissolved in 1 ml of methyl methacrylate. The resulting solution was introduced into a Pyrex® glass tube. Then, the glass tube was subjected to vacuum degassing ($10^{-3}$ Torr) and then sealed. The glass tube thus obtained was placed in a constant-temperature bath having a temperature of 60° C. (five-hour-long reaction), and a polymerization reaction of methyl methacrylate was performed. After the polymerization reaction, a sample (polymethyl methacrylate containing a europium complex) was taken out from the glass tube. A measuring sample was prepared by optically polishing the sample with $Al_2O_3$ nanoparticles.

Example of Experiment for Optical Measurement

The following describes an example of experiment to perform optical measurement of the resin caused to contain a europium ion. However, the present invention is not limited to the following example of experiment, and only needs to use a method capable of measuring spectral intensity at a desired wavelength.

In optically measuring a polymer sample containing a europium ion, a fluorescence spectroscopic apparatus (HITACHI F-4500) was used. The light obtained from the sample was measured with use of the fluorescence spectroscopic apparatus with the excitation wavelength set at 465 nm. The emission spectrum thus obtained through the measurement was corrected in accordance with a function of the detection sensitivity and lamp intensity of the measuring apparatus. Furthermore, the emission spectrum was standardized with the emission component (magnetic dipole transition) set to be 1 at 590 nm (FIG. 2).

As described above, an information identification device according to the present invention includes: a light source for irradiating, with exciting light, a light-emitting member containing a rare-earth complex; a measurement section for receiving light emitted from the light-emitting member, and for measuring intensities (spectral intensities) of the light; a computation section for computing a ratio of light intensities (spectral intensities) at a plurality of different wavelengths among the light intensities (spectral intensities) thus measured; and an identification section for identifying identification information corresponding to the ratio thus computed.

Further, as described above, an information identification method according to the present invention includes: an irradiating step of irradiating, with exciting light, a light-emitting member containing a rare-earth complex; a measuring step of receiving light emitted from the light-emitting member, and of measuring intensities (spectral intensities) of the light; a computing step of computing a ratio of light intensities (spectral intensities) at a plurality of different wavelengths among the light intensities (spectral intensities) thus measured; and an identifying step of identifying identification information corresponding to the ratio thus computed.

Further, as described above, an information identification system according to the present invention includes (i) a light-emitting member containing a rare-earth complex and (ii) an information identification device for identifying identification information corresponding to the rare-earth complex, the information identification device including: a light source for irradiating, with exciting light, a light-emitting member containing a rare-earth complex; a measurement section for receiving light emitted from the light-emitting member, and for measuring intensities (spectral intensities) of the light; a computation section for computing a ratio of light intensities (spectral intensities) at a plurality of different wavelengths among the light intensities (spectral intensities) thus measured; and an identification section for identifying identification information corresponding to the ratio thus computed.

According to the foregoing arrangement, the light-emitting member contains a rare-earth complex. For this reason, the light-emitting member emits light when the light source irradiates the light-emitting member with exciting light. The measurement section receives the light emitted from the light-emitting member and measures intensities (spectral intensities) of the light. Further, the computation section computes a ratio of light intensities (spectral intensities) at a plurality of different wavelengths among the light intensities (spectral intensities) thus measured. That is, the computation section computes a ratio of light intensities at specific wavelengths. Then, the identification section identifies identification information corresponding to the ratio thus computed.

This makes it possible to specify the rare-earth complex contained in the light-emitting member, thereby bringing about an effect of providing an information identification device, an information identification method, and an information identification system each of which has an unprecedentedly high level of identifying power (security).

In other words, the information identification device according to the present invention includes: a light source for irradiating, with exciting light, a light-emitting member containing a rare-earth complex; a measurement section for receiving light emitted from the light-emitting member, and for measuring intensities of the light; a computation section for computing a ratio of intensities of light at a plurality of different wavelengths among the light intensities thus measured; and an identification section for identifying identification information corresponding to the ratio thus computed.

According to the foregoing arrangement, the light-emitting member contains a rare-earth complex. For this reason, the light-emitting member emits light when the light source irradiates the light-emitting member with exciting light. The measurement section receives the light emitted from the light-emitting member and measures intensities of the light. Further, the computation section computes a ratio of intensities of the light at different wavelengths among the light intensities thus measured. That is, the computation section computes a ratio of light intensities at specific wavelengths. Then, the identification section identifies identification information corresponding to the ratio thus computed.

Thus, the present invention identifies the identification information corresponding to the rare-earth complex. That is, in general, a rare-earth complex has a plurality of emission peaks, and the light intensity ratio of the peaks is a value unique to the rare-earth complex. For this reason, the rare-earth complex contained in the light-emitting member can be specified (identified) by computing the ratio of light intensities at a plurality of different wavelengths among the light emitted from the rare-earth complex. This makes it possible to identify and authenticate the identification information corresponding to the rare-earth complex. Thus, the rare-earth complex contained in the light-emitting member can be specified. This makes it possible to provide an information identification device having an unprecedentedly high level of identifying power (security).

The "light at a plurality of wavelengths" also means "a plurality of beams of light at different wavelengths". Therefore, "to compute a ratio of intensities of light at a plurality of wavelengths" means "to compute a ratio of intensities of two or more beams of light at different wavelengths". That is, in this case, the computation section may compute a ratio of intensities of light at two wavelengths, a ratio of intensities of light at three wavelengths, or a ratio of intensities of light at four or more wavelengths. This can be appropriately set in accordance with the number of emission peaks of a rare-earth complex.

Further, since the present invention specifies a substance in accordance with a light intensity ratio, the substance can be specified even in cases where the rare-earth complex has deteriorated. There are no restrictions on use conditions such as temperature, either. Further, the rare-earth complex is transparent and colorless and therefore invisible when not in use (when not irradiated with exciting light), thereby ensuring a higher level of security. Furthermore, the use of a single rare-earth ion makes it possible to recover used rare-earth ions, which are precious resources.

The information identification device according to the present invention is preferably arranged such that the computation section computes a ratio between an intensity of first-wavelength light and an intensity of second-wavelength light. The first-wavelength light and the second-wavelength light refer to those beams of light at specific wavelengths which are contained in the light emitted from the light-emitting member, and to beams of light at wavelengths that are measured for the purpose of computing a light intensity ratio.

These beams of light at respective wavelengths are appropriately set in accordance with the emission distribution of the rare-earth complex, and are preferably at any of the plurality of emission peaks. Thus, the ratio is computed in accordance with the intensities of light at two specific wavelengths. This not only makes it possible to specify the rare-earth complex, but also makes it easy to perform the computation.

The information identification device according to the present invention is preferably arranged so as to include a plurality of wavelength selection sections for transmitting beams of light at specific wavelengths among the light emitted from the light-emitting member, respectively, wherein the measurement section receives the beams of light respectively transmitted by the wavelength selection sections and measures respective intensities of the beams of light.

According to the foregoing arrangement, the wavelength selection sections are provided. Each of the wavelength selection sections transmits that beam of light at a specific wavelength which is contained in the light emitted from the light-emitting member. Further, the wavelength selection sections are provided for beams of light at different wavelengths, respectively. This makes it possible to use the wavelength selection sections to transmit those beams of light at different wavelengths which are contained in the light emitted from the light-emitting member, respectively.

The beams of light respectively transmitted by the wavelength selection sections are beams of light at wavelengths that are measured for the purpose of computing a light intensity ratio. That is, the measurement section receives the beams of light respectively transmitted by the wavelength selection sections and measures respective intensities of the beams of light.

Thus, in cases where the wavelengths for computing a light intensity ratio are predetermined, the provision of wavelength selection sections for respective wavelengths makes it only necessary for the measurement section to measure only light intensity at each wavelength. This makes it possible to increase the speed of processing, and to provide an information identification device having a higher level of identifying power (security).

The information identification device according to the present invention is preferably arranged such that: the plurality of wavelength selection sections include a first wavelength selection section for transmitting first-wavelength light emitted from the light-emitting member and a second wavelength selection section for transmitting second-wavelength light emitted from the light-emitting member; the measurement section receives the first-wavelength light and the second-wavelength light and measures respective intensities of the first-wavelength light and the second-wavelength light; and the computation section computes a ratio between the intensity of the first-wavelength light and the intensity of the second-wavelength light.

According to the foregoing arrangement, the wavelength selection sections include the first wavelength selection section and the second wavelength selection section. The first wavelength selection section transmits the first-wavelength light emitted from the light-emitting member. Further, the second wavelength selection section transmits the second-wavelength light emitted from the light-emitting member. The first-wavelength light and the second-wavelength light refer to those beams of light at specific wavelengths which are contained in the light emitted from the light-emitting member, and to beams of light at wavelengths that are measured for the purpose of computing a light intensity ratio.

The measurement section receives the first-wavelength light and the second-wavelength light and measures the respective intensities of the first-wavelength light and the second-wavelength light. Further, the computation section computes the ratio between the intensity of the first-wavelength light and the intensity of the second-wavelength light. That is, the computation section computes a ratio of light intensities at two wavelengths for computing a light intensity ratio. Moreover, the identification section identifies the identification information corresponding to the ratio thus computed.

Thus, in cases where the two wavelengths for computing a light intensity ratio are determined, the provision of wavelength selection sections for respective wavelengths makes it only necessary for the measurement section to measure only light intensity at each wavelength. Further, the computation section does not need to extract light intensities at specific wavelengths from among all wavelengths, and can compute a ratio by using only the light intensities thus measured by the measurement section. This makes it possible to increase the speed of processing, and to provide an information identification device having a higher level of identifying power (security).

The information identification device according to the present invention is preferably arranged such that: the light-emitting member contains plural types of rare-earth complex; and the computation section computes a ratio of light intensities at wavelengths corresponding to each rare-earth complex.

According to the foregoing arrangement, each of the rare-earth complexes contained in the light-emitting member emits light. Moreover, the computation section computes a ratio of light intensities at wavelengths corresponding light emitted from each rare-earth complex. That is, although wavelengths for computing a ratio vary from one rare-earth complex to another, the computation section computes a ratio in accordance with light intensities at wavelengths for specifying each rare-earth complex. Therefore, even in cases where the plural types of rare-earth complex are used, each of the rare-earth complexes can be specified. This makes it possible to provide an information identification device having a higher level of identifying power (security).

An information identification method according to the present invention includes: an irradiating step of irradiating, with exciting light, a light-emitting member containing a rare-earth complex; a measuring step of receiving light emitted from the light-emitting member, and of measuring intensities of the light; a computing step of computing a ratio of intensities of light at a plurality of different wavelengths among the light intensities thus measured; and an identifying step of identifying identification information corresponding to the ratio thus computed.

According to the foregoing arrangement, in the irradiating step, the light-emitting member containing a rare-earth complex is irradiated with exciting light. This causes the light-emitting member to emit light. In the measurement step, the light thus emitted is received, and the intensities of the light are measured. Furthermore, in the computing step, the ratio of intensities of light at a plurality of different wavelengths among the light intensities thus measured is computed. Then, in the identifying step, the identification information corresponding to the ratio thus computed is identified.

Thus, in the present invention, the rare-earth complex contained in the light-emitting member can be specified (identified) by computing the ratio of light intensities at a plurality of different wavelengths among the light emitted from the rare-earth complex, and the identification information corresponding to the rare-earth complex is identified and authenticated. Thus, since the present can specify the rare-earth complex contained in the light-emitting member, the present invention provides an information identification method having an unprecedentedly high level of identifying power (security).

Further, since the present invention specifies a substance in accordance with a light intensity ratio, the substance can be specified even in cases where the rare-earth complex has deteriorated. There are no restrictions on use conditions such as temperature, either. Further, the rare-earth complex is transparent and colorless and therefore invisible when in a normal state, thereby ensuring a higher level of security. Furthermore, the use of a single rare-earth ion makes it possible to recover used rare-earth ions, which are precious resources.

The information identification method according to the present invention is preferably arranged such that in the computing step, a ratio between an intensity of first-wavelength light and an intensity of second-wavelength light among the intensities of light thus measured is computed. According to the foregoing arrangement, the ratio is computed in accordance with the intensities of light at two specific wavelengths. This not only makes it possible to specify the rare-earth complex, but also makes it easy to perform the computation.

The information identification method according to the present invention is preferably arranged so as to carry out wavelength selecting steps of transmitting beams of light at specific wavelengths among the light emitted from the light-emitting member, respectively, wherein in the measuring step, the beams of light respectively transmitted are received and respective intensities of the beams of light are measured.

Thus, in cases where the wavelengths for computing a light intensity ratio are predetermined, the provision of wavelength selection sections for respective wavelengths makes it only necessary for the measurement section to measure only light intensity at each wavelength. This makes it possible to increase the speed of processing, and to provide an information identification method having a higher level of identifying power (security).

The information identification method according to the present invention is preferably arranged such that: the wavelength selecting steps include a first wavelength selecting step of transmitting first-wavelength light emitted from the light-emitting member and a second wavelength selecting step of transmitting second-wavelength light emitted from the light-emitting member; in the measuring step, the first-wavelength light and the second-wavelength light are received and respective intensities of the first-wavelength light and the second-wavelength light are measured; and in the computing step, a ratio between the intensity of the first-wavelength light and the intensity of the second-wavelength light is measured.

Furthermore, in cases where two wavelengths for computing a light intensity ratio are determined, the provision of wavelength selection sections for respective wavelengths makes it only necessary for the measurement section to measure only light intensity at each wavelength. Further, in this case, the computation section does not need to extract light intensities at specific wavelengths from among all wavelengths, and can compute a ratio by using only the light intensities thus measured by the measurement section. This makes it possible to increase the speed of processing, and to provide an information identification method having a higher level of identifying power (security).

The information identification method according to the present invention is preferably arranged such that: the light-emitting member contains plural types of rare-earth complex; and the computing step computes a ratio of light intensities at wavelengths corresponding to each rare-earth complex. According to the foregoing arrangement, even in cases where the plural types of rare-earth complex are used, each of the rare-earth complexes can be specified. This makes it possible to provide an information identification method having a higher level of identifying power (security).

An information identification system includes (i) a light-emitting member containing a rare-earth complex and (ii) an information identification device for identifying identification information corresponding to the rare-earth complex, the information identification device including: a light source for irradiating, with exciting light, a light-emitting member containing a rare-earth complex; a measurement section for receiving light emitted from the light-emitting member, and for measuring intensities of the light; a computation section for computing a ratio of intensities of light at a plurality of different wavelengths among the light intensities thus measured; and an identification section for identifying identification information corresponding to the ratio thus computed.

As with the information identification device already explained, the foregoing arrangement can provides an information identification system having an unprecedentedly high level of identifying power (security). Further, since a substance is specified (identified) in accordance with a light intensity ratio, the substance can be specified even in cases where the rare-earth complex has deteriorated. There are no restrictions on use conditions such as temperature, either.

Further, the rare-earth complex is transparent and colorless and therefore invisible when in a normal state, thereby ensuring a higher level of security. Furthermore, the use of a single rare-earth ion makes it possible to recover used rare-earth ions, which are precious resources. Further, the information identification system has a simple arrangement. This makes it possible to reduce the cost of the system.

In cases where the light-emitting member contains plural types of rare-earth complex, the number of available pieces of identification information (number of pieces of information that can be encrypted) can be increased. That is, in this case, an information identification system having a vast amount of identification information can be provided.

A light-emitting member according to the present invention is a light-emitting member, containing a rare-earth complex, which can be identified by an information identification device including: a light source for irradiating, with exciting light, a light-emitting member containing a rare-earth complex; a measurement section for receiving light emitted from the light-emitting member, and for measuring intensities (spectral intensities) of the light; a computation section for computing a ratio of light intensities (spectral intensities) at a plurality of different wavelengths among the light intensities (spectral intensities) thus measured; and an identification section for identifying identification information corresponding to the ratio thus computed.

According to the foregoing arrangement, the light-emitting member contains a rare-earth complex, and can be identified by the information identification device, which serves as a device that identifies identification information in accordance with the ratio of light intensities (spectral intensities) at a plurality of different wavelengths among the light thus emitted. This makes it possible to provide a light-emitting member that is used for an information identification device having an unprecedentedly high level of identifying power (security). For this reason, the light-emitting member can be referred to as "member to be identified".

The present invention is not limited to the description of the embodiments above, but may be altered by a skilled person within the scope of the claims. An embodiment based on a proper combination of technical means disclosed in different embodiments is encompassed in the technical scope of the present invention.

INDUSTRIAL APPLICABILITY

An information identification method of the present invention identifies and authenticates an ID by identifying (specifying) a rare-earth complex by calculating the ratio of spectral intensities of light emitted from an ID identifying medium at a plurality of wavelengths. For this reason, an information identification device of the present invention and an information identification system of the present invention can be suitably used for an ID identification and authentication system, a security system, and the like.

The invention claimed is:

1. An information identification device comprising:
a light source for irradiating, with exciting light, a light-emitting member containing a rare-earth complex;
a measurement section for receiving light emitted from the light-emitting member, and for measuring spectral intensities of the light;
a computation section for computing a ratio of spectral intensities at a plurality of different wavelengths among the spectral intensities thus measured; and
an identification section for identifying identification information corresponding to the ratio thus computed,
wherein the computation section computes a ratio between an intensity of spectra containing a first-wavelength line spectrum based on magnetic dipole transition and an intensity of spectra containing a second-wavelength line spectrum based on electric dipole transition among the spectral intensities measured by the measurement section.

2. The information identification device as set forth in claim 1, further comprising:
a wavelength selection section for splitting, into the spectra containing the first-wavelength line spectrum and the spectra containing the second-wavelength line spectrum, the light emitted from the light-emitting member, wherein
the measurement section measures intensities of the spectra into which the light emitted from the light-emitting member has been split by the wavelength selection section.

3. The information identification device as set forth in claim 2, wherein the wavelength selection section splits, by transmission, reflection, diffraction, or refraction, the light emitted from the light-emitting member.

4. The information identification device as set forth in claim 1, wherein:
   the light-emitting member contains plural types of rare-earth complex; and
   the computation section computes a ratio of spectral intensities at a plurality of wavelengths corresponding to each rare-earth complex.

5. An information identification method comprising:
   an irradiating step of irradiating, with exciting light, a light-emitting member containing a rare-earth complex;
   a measuring step of receiving light emitted from the light-emitting member, and of measuring spectral intensities of the light;
   a computing step of computing a ratio of spectral intensities at a plurality of different wavelengths among the spectral intensities thus measured; and
   an identifying step of identifying identification information corresponding to the ratio thus computed,
   wherein the computing step computes a ratio between an intensity of spectra containing a first-wavelength line spectrum based on magnetic dipole transition and an intensity of spectra containing a second-wavelength line spectrum based on electric dipole transition among the spectral intensities thus measured.

6. The information identification method as set forth in claim 5, further comprising:
   a wavelength selecting step of splitting, into the spectra containing the first-wavelength line spectrum and the spectra containing the second-wavelength line spectrum, the light emitted from the light-emitting member, wherein
   the measuring step measures intensities of the spectra into which the light emitted from the light-emitting member has been split by the wavelength selection section.

7. The information identification method as set forth in claim 6, wherein the wavelength selecting step splits, by transmission, reflection, diffraction, or refraction, the light emitted from the light-emitting member.

8. The information identification method as set forth in claim 5, wherein:
   the light-emitting member contains plural types of rare-earth complex; and
   the computing step computes a ratio of spectral intensities at a plurality of wavelengths corresponding to each rare-earth complex.

9. An information identification system including (i) a light-emitting member containing a rare-earth complex and (ii) an information identification device for identifying identification information corresponding to the rare-earth complex, the information identification device comprising:
   a light source for irradiating, with exciting light, a light-emitting member containing a rare-earth complex;
   a measurement section for receiving light emitted from the light-emitting member, and for measuring spectral intensities of the light;
   a computation section for computing a ratio of spectral intensities at a plurality of different wavelengths among the spectral intensities thus measured; and
   an identification section for identifying identification information corresponding to the ratio thus computed,
   wherein the computation section computes a ratio between an intensity of spectra containing a first-wavelength line spectrum based on magnetic dipole transition and an intensity of spectra containing a second-wavelength line spectrum based on electric dipole transition among the spectral intensities measured by the measurement section.

10. The information identification device as set forth in claim 4, wherein the plural types of rare-earth complex are complexes including a same rare-earth ion and different combinations of ligands coordinated therearound.

11. The information identification method as set forth in claim 8, wherein the plural types of rare-earth complex are complexes including a same rare-earth ion and different combinations of ligands coordinated therearound.

12. The information identification device as set forth in claim 9, wherein:
   the light-emitting member contains plural types of rare-earth complex; and
   the plural types of rare-earth complex are complexes including a same rare-earth ion and different combinations of ligands coordinated therearound.

* * * * *

UNITED STATES PATENT AND TRADEMARK OFFICE
CERTIFICATE OF CORRECTION

PATENT NO.        : 7,796,242 B2
APPLICATION NO.   : 11/990604
DATED             : September 14, 2010
INVENTOR(S)       : Yasuchika Hasegawa and Tsuyoshi Kawai It is certified that error appears in the above-identified patent and that said Letters Patent is hereby corrected as shown below:

Title Page, item (73) should read
(73) Assignees: National University Corporation Nara Institute of Science and Technology, Ikoma-Shi Nara(JP)

Signed and Sealed this
Fourth Day of January, 2011

David J. Kappos
*Director of the United States Patent and Trademark Office*